(12) United States Patent
Kim et al.

(10) Patent No.: US 12,364,808 B2
(45) Date of Patent: Jul. 22, 2025

(54) LIQUID MEDICINE INJECTION DEVICE

(71) Applicant: IPV, Seoul (KR)

(72) Inventors: Kiung Kim, Incheon (KR); Wonkyung Bang, Seoul (KR); Daejong Park, Seoul (KR); Seungha Kim, Goyang-si (KR)

(73) Assignee: IPV, Seoul (KR)

( * ) Notice: Subject to any disclaimer, the term of this patent is extended or adjusted under 35 U.S.C. 154(b) by 0 days.

(21) Appl. No.: 18/610,192

(22) Filed: Mar. 19, 2024

(65) Prior Publication Data

US 2024/0226427 A1    Jul. 11, 2024

Related U.S. Application Data

(63) Continuation of application No. 18/116,616, filed on Mar. 2, 2023, now Pat. No. 11,964,128, which is a
(Continued)

(30) Foreign Application Priority Data

Sep. 7, 2020   (KR) .................. 10-2020-0114094
Sep. 7, 2020   (KR) .................. 10-2020-0114117
(Continued)

(51) Int. Cl.
*A61M 5/142*    (2006.01)
*A61M 5/158*    (2006.01)
(Continued)

(52) U.S. Cl.
CPC ........ *A61M 5/14248* (2013.01); *A61M 5/158* (2013.01); *A61M 5/1723* (2013.01);
(Continued)

(58) Field of Classification Search
CPC .............. A61M 5/14248; A61M 5/158; A61M 5/1723; A61M 5/31573;
(Continued)

(56) References Cited

U.S. PATENT DOCUMENTS 4,573,994 A       3/1986   Fischell et al.
5,053,019 A  *   10/1991   Duffy .................. A61M 5/1785
                                                              600/432
(Continued)

FOREIGN PATENT DOCUMENTS

JP       2006068509 A     3/2006
JP         5247701 B2     7/2013
(Continued)

OTHER PUBLICATIONS

Notice of Non-Final Rejection dated Apr. 29, 2022, issued in Korean Patent Application No. 10-2020-0114117.
(Continued)

*Primary Examiner* — James D Ponton
(74) *Attorney, Agent, or Firm* — PnK IP LLC

(57) ABSTRACT

A medical liquid injection device is provided. The medical liquid injection device includes a base body, a needle assembly mounted on the base body, a reservoir fluidly connected to the needle assembly and having a guide groove on an inner surface, and a driving unit configured to move a plunger disposed inside the reservoir.

2 Claims, 30 Drawing Sheets

Related U.S. Application Data continuation of application No. PCT/KR2021/011186, filed on Aug. 23, 2021.

(30) Foreign Application Priority Data

Sep. 7, 2020 (KR) .................. 10-2020-0114131
Sep. 7, 2020 (KR) .................. 10-2020-0114132

(51) Int. Cl.
*A61M 5/172* (2006.01)
*A61M 5/315* (2006.01)

(52) U.S. Cl.
CPC . *A61M 5/31573* (2013.01); *A61M 2202/0486* (2013.01); *A61M 2205/3303* (2013.01)

(58) Field of Classification Search
CPC .. A61M 2202/0486; A61M 2205/3303; A61M 5/001; A61M 2005/1402; A61M 5/172; A61M 5/36; A61M 2005/14252; A61M 2005/3114; A61M 2230/201; A61M 5/14244; A61M 5/2066; A61M 5/2448; A61M 5/284; A61M 5/31596; A61M 5/3294

See application file for complete search history.

(56) References Cited

U.S. PATENT DOCUMENTS

| | | |
|---|---|---|
| 10,420,883 B2 | 9/2019 | Diianni et al. |
| 2002/0123740 A1 | 9/2002 | Flaherty et al. |
| 2003/0088216 A1 | 5/2003 | Py |
| 2008/0306444 A1* | 12/2008 | Brister .............. A61B 5/14546 604/131 |
| 2017/0312441 A1 | 11/2017 | Draper et al. |
| 2018/0272058 A1* | 9/2018 | Pizzochero ....... A61M 5/14248 |
| 2019/0091408 A1 | 3/2019 | Kim et al. |
| 2020/0206417 A1 | 7/2020 | Yodfat et al. |

FOREIGN PATENT DOCUMENTS

| | | |
|---|---|---|
| JP | 2017104821 A | 6/2017 |
| JP | 6280376 B2 | 2/2018 |
| JP | WO2017002870 A1 | 4/2018 |
| JP | 2020018493 A | 2/2020 |
| KR | 10-1802110 B1 | 11/2017 |
| KR | 10-2020-0019528 A | 2/2020 |
| KR | 102144192 B1 | 8/2020 |
| WO | 2016/132937 | 8/2016 |
| WO | 2017064483 A1 | 4/2017 |
| WO | 2019/231713 | 12/2019 |
| WO | 2020036402 | 2/2020 |

OTHER PUBLICATIONS

Notice of Allowance dated Jan. 20, 2023, issued in Korean Patent Application No. 10-2020-0114117.
Extended European Search Report dated Jan. 16, 2024, issued in European Patent Application No. 21864574.5.
Notice of Reasons for Refusal issued on Jan. 23, 2024 for Japanese Application No. 2023-515208.
Notice of Reasons for Refusal issued on May 7, 2024 for Japanese Application No. 2023-515208.
Decision to Grant a Patent issued on Aug. 13, 2024 for Japanese Application No. 2023-515208.

* cited by examiner

LIQUID MEDICINE INJECTION DEVICE

CROSS-REFERENCE TO RELATED APPLICATIONS

This application is a Continuation Application of U.S. application Ser. No. 18/116,616, filed on Mar. 2, 2023, which is a Continuation Application of International Patent Application No. PCT/KR2021/011186, filed on Aug. 23, 2021, which claims priority to Korean Patent Application No. 10-2020-0114094, filed on Sep. 7, 2020, Korean Patent Application No. 10-2020-0114117, filed on Sep. 7, 2020, Korean Patent Application No. 10-2020-0114131, filed on Sep. 7, 2020, and Korean Patent Application No. 10-2020-0114132, filed on Sep. 7, 2020, each of which is hereby incorporated by reference for all purposes as if fully set forth herein.

BACKGROUND

Field

The present disclosure relates to a medical liquid injection device.

Discussion of the Background

In general, medical liquid injection devices such as insulin injection devices are used to inject medical liquids into patients' bodies. Although the medical liquid injection devices are sometimes used by professional medical staff such as doctors or nurses, in most cases, it is used by general public such as the patients themselves or guardians.

Diabetic patients, especially pediatric diabetic patients, need to inject medical liquids such as insulin into the body at regular intervals. A medical liquid injection device in the form of a patch to be used by being attached to the human body for a certain period of time is being developed, and such a medical liquid injection device may be used while being attached to the body part like the abdomen or the waist of a patient for a certain period of time.

To improve the effect through medical liquid injection, a medical liquid injection device needs to precisely control the injection of a medical liquid into a patient's body, and it is important to precisely inject a small amount of a medical liquid through a small medical liquid injection device.

It is necessary to have excellent wearability when the medical liquid injection device is attached to the human body, convenient use, excellent durability, and low power consumption. In particular, since the medical liquid injection device is used by being directly attached to a patient's skin, it is important to allow a user to drive the medical liquid injection device conveniently and safely.

SUMMARY

The present disclosure provides a medical liquid injection device capable of accurately delivering a medical liquid.

According to an aspect of the present disclosure, a medical liquid injection device includes a base body, a needle assembly mounted on the base body, a reservoir fluidly connected to the needle assembly and having a guide groove on an inner surface, and a driving unit configured to move a plunger disposed inside the reservoir.

According to an aspect of the present disclosure, a medical liquid injection device includes a base body, a needle assembly mounted on the base body, a reservoir fluidly connected to the needle assembly and having an inlet end into which a medical liquid is injected, a sealing member attached to the inlet end, and a guide cap attached to the base body or the reservoir to face the sealing member.

According to an aspect of the present disclosure, a medical liquid injection device includes a base body, a needle assembly mounted on the base body, a reservoir fluidly connected to the needle assembly and having a plunger therein, a rod connected to the plunger and including a male screw having a first screw thread and a first screw groove on an outer circumferential surface, and a connecting member including a female screw having a second screw thread and a second screw groove on at least a portion of an inner circumferential surface, wherein the rod contacts the female screw of the connecting member only in outer regions in a radial direction at the center of a height between the first screw thread and the first screw groove.

According to an aspect of the present disclosure, a medical liquid injection device includes a base body, a reservoir attached to the base body and having a plunger disposed therein, a rod connected to the plunger, a connecting member into which the rod is inserted, a drive wheel disposed to be apart from one end of the reservoir and transmitting a driving force to the connecting member, and a resistance member inserted into the connecting member and disposed between the reservoir and the drive wheel.

A medical liquid injection device according to an embodiment of the present disclosure may safely inject a medical liquid into a user. The medical liquid injection device may remove a gas from a reservoir and safely store a medical liquid in the reservoir, thereby eliminating the risk of injecting gas into the user. The medical liquid injection device may discharge a gas discharged through a needle to the outside to improve safety and indicate whether a medical liquid is stored therein.

The medical liquid injection device according to an embodiment of the present disclosure may guide an injection needle to be inserted precisely into a pre-set position to inject a medical liquid, thereby safely storing the medical liquid in the reservoir.

In the medical liquid injection device according to an embodiment of the present disclosure, when the injection needle is inserted to inject a medical liquid, foreign substances are not generated due to scratches, and thus high safety of the medical liquid injection device may be secured.

The medical liquid injection device according to an embodiment of the present disclosure may minimize contact with foreign substances, and a user may easily insert the injection needle of a medical liquid injector into the reservoir.

In the medical liquid injection device according to an embodiment of the present disclosure, a path through which a sterilization gas moves is set for disinfection, and thus the safety of the medical liquid injection device may be improved.

The medical liquid injection device according to an embodiment of the present disclosure may accurately discharge a fixed amount of the medical liquid. In the medical liquid injection device, a driving force generated by a driving module is accurately transmitted to a plunger, and thus a fixed amount of a medical liquid may be discharged through a needle.

In the medical liquid injection device according to an embodiment of the present disclosure, the plunger may linearly move even by a small driving force. A rod connected to the plunger is screw-coupled to the connecting member. However, the contact area between a male screw of the rod and a female screw of the connecting member is reduced, and thus the rod may linearly move even when a small driving force rotates the connecting member. Since a convex curvature is formed at a screw thread or a concave curvature is formed at a screw groove in the male screw of the rod and the female screw of the connecting member, the contact area between the female screw and the male screw may be reduced to reduce frictional force, and thus the rod may linearly move even when a small driving force is transmitted to the connecting member.

The medical liquid injection device according to the present disclosure may store a high-pressure medical liquid in a reservoir. Since the medical liquid stored in the reservoir is stored at a high pressure, even when a small driving force is applied to the plunger, the plunger may move forward to quickly discharge a fixed amount of the medical liquid.

The medical liquid injection device according to the present disclosure may quickly inject a medical liquid into a user without a delay in discharging of the medical liquid through a needle. The medical liquid stored at a high pressure may be discharged through the needle even when a small driving force is applied to the plunger. Therefore, when the medical liquid injection device is attached to a user, the medical liquid may be immediately injected into the user. Of course, the scope of the present disclosure is not limited by these effects.

DETAILED DESCRIPTION

Figure 1:
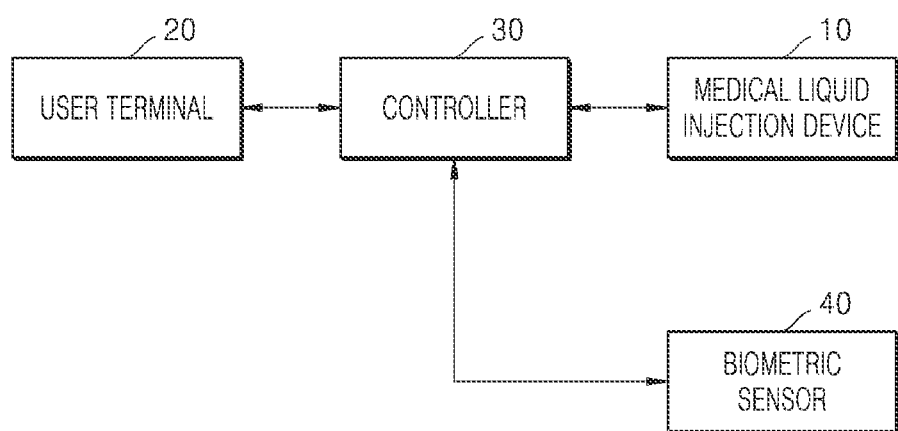
FIG. 1 is a block diagram illustrating a medical liquid injection system according to an embodiment of the present disclosure.

According to an aspect of the present disclosure, a medical liquid injection device includes a base body, a needle assembly mounted on the base body, a reservoir fluidly connected to the needle assembly and having a guide groove on an inner surface, and a driving unit configured to move a plunger disposed inside the reservoir.

Also, the reservoir may have an inlet end through which a medical liquid is injected and an outlet end connected to a needle of the needle assembly, and the guide groove may interconnect the inlet end and the outlet end.

Also, the guide groove may guide a gas remaining in an inner space of the reservoir to the needle assembly when a medical liquid is injected into the reservoir.

Also, a portion of the guide groove may be inclined along an inner surface of the reservoir.

According to another aspect of the present disclosure, a reservoir for a medical liquid injection device, in which a medical liquid is stored in an inner space and the medical liquid is discharged through a needle by movement of a plunger, the reservoir includes an inlet end through which the medical liquid is injected, an outlet end at which the needle is installed, and a guide groove disposed on an inner surface of the reservoir, wherein at least a portion of the guide groove interconnects the inlet end and the outlet end.

According to another aspect of the present disclosure, a medical liquid injection device includes a base body, a needle assembly mounted on the base body, a reservoir fluidly connected to the needle assembly and having an inlet end into which a medical liquid is injected, a sealing member attached to the inlet end, and a guide cap attached to the base body or the reservoir to face the sealing member.

Also, the guide cap may include a flange attached to a seating end of the base body and an inclined end extending inwardly from the flange with a reduced open cross-sectional area.

Also, the guide cap may further include wing pieces extending outwardly from the flange and supported by the base body.

Also, the guide cap may have a curved surface in a region where the flange and the inclined end are connected to each other.

Also, the guide cap may be inserted to a pre-set depth from the surface of the base body.

According to another aspect of the present disclosure, a medical liquid injection device includes a base body, a needle assembly mounted on the base body, a reservoir fluidly connected to the needle assembly and having a plunger therein, a rod connected to the plunger and including a male screw having a first screw thread and a first screw groove on an outer circumferential surface, and a connecting member including a female screw having a second screw thread and a second screw groove on at least a portion of an inner circumferential surface, wherein the rod contacts the female screw of the connecting member only in outer regions in a radial direction at the center of a height between the first screw thread and the first screw groove.

Also, the rod has a distance between the first screw threads adjacent to each other as a pitch and a distance between the first screw threads and the first screw groove as a first height, wherein the first height may be set to be 50% or less of the pitch.

Also, the first height between the first screw thread and the first screw groove may be smaller than a second height between the second screw thread and the second screw groove.

Also, the first screw thread has a first curvature radius, the first screw groove has a second curvature radius, the second screw thread has a third curvature radius, and the second screw groove has a fourth curvature radius, wherein at least one of the first curvature radius and the second curvature radius may be different from the third curvature radius and different from the fourth curvature radius.

Also, at least one of the first curvature radius and the second curvature radius may be between the third curvature radius and the fourth curvature radius.

According to another aspect of the present disclosure, a medical liquid injection device includes a base body, a reservoir attached to the base body and having a plunger disposed therein, a rod connected to the plunger, a connecting member into which the rod is inserted, a drive wheel disposed to be apart from one end of the reservoir and transmitting a driving force to the connecting member, and a resistance member inserted into the connecting member and disposed between the reservoir and the drive wheel.

Also, when the plunger and the connecting member move toward the rear of the reservoir, one side of the resistance member may be supported by the driving wheel.

Also, the resistance member may generate frictional force with the outer circumferential surface of the connecting member.

Also, the resistance member may have an insertion opening into which the connecting member is inserted, wherein a minimum diameter of the insertion opening may be smaller than a diameter of the connecting member.

Also, the resistance member may have a base portion extending outwardly of the insertion opening into which the connecting member is inserted and a cutout formed at one side of the base portion and connected to the insertion opening.

Since the present disclosure can apply various transformations and can have various embodiments, specific embodiments are illustrated in the drawings and described in detail in the detailed description. Effects and features of the present disclosure, and a method of achieving them will become clear with reference to the embodiments described below in detail in conjunction with the drawings. However, the present disclosure is not limited to the embodiments disclosed below and may be implemented in various forms.

Hereinafter, embodiments of the present disclosure will be described in detail with reference to the accompanying drawings, and when described with reference to the drawings, the same or corresponding components are given the same reference numerals, and overlapping descriptions thereof will be omitted.

In the following examples, the singular expression includes the plural expression unless the context clearly dictates otherwise.

In the following embodiments, terms such as include or have means that the features or components described in the specification are present, and the possibility that one or more other features or components will be added is not excluded in advance.

In cases where certain embodiments may be implemented otherwise, a specific process sequence may be performed differently from the described sequence. For example, two processes described in succession may be performed substantially simultaneously or may be performed in an order opposite to the order described.

In the drawings, the size of the components may be exaggerated or reduced for convenience of description. For example, since the size and thickness of each component shown in the drawings are arbitrarily indicated for convenience of description, embodiments below are not necessarily limited to those illustrated.

FIG. 1 is a block diagram illustrating a medical liquid injection system 1 according to an embodiment of the present disclosure.

Referring to FIG. 1, the medical liquid injection system 1 may include a medical liquid injection device 10, a user terminal 20, a controller 30 and a biometric sensor 40. In the medical liquid injection system 1, a user is capable of driving and controlling the medical liquid injection system 1 by using the user terminal 20, and, based on blood glucose information monitored by the biometric sensor 40, the medical liquid injection device 10 may periodically inject a medical liquid.

The medical liquid injection device 10 also performs a function of injecting a medical liquid that needs to be injected to ta user, e.g., insulin, glucagon, anesthetics, painkillers, dopamine, growth hormone, and smoking cessation aid, based on data sensed by the biometric sensor 40.

Also, the medical liquid injection device 10 may transmit a device status message including information regarding the remaining battery capacity of the medical liquid injection device 10, a result (success or failure) of booting of the medical liquid injection device 10, a result (success or failure) of injection, etc., to the controller 30. Messages transmitted to the controller may be transmitted to the user terminal 20 via the controller 30. Alternatively, the controller 30 may transmit enhanced data obtained by processing received messages to the user terminal 20.

According to an embodiment, the medical liquid injection device 10 may be provided separately from the biometric sensor 40 and may be installed to be spaced apart from a target object. According to another embodiment, the medical liquid injection device 10 and the biometric sensor 40 may be provided within a single device.

According to an embodiment, the medical liquid injection device 10 may be attached to a user's body. Also, according to another embodiment, the medical liquid injection device 10 may be attached to an animal to inject a medical liquid into the body of the animal.

The user terminal 20 may receive an input signal from a user to drive and control the medical liquid injection system 1. The user terminal 20 may generate a signal for driving the controller 30 and control the controller 30 to drive the medical liquid injection device 10. Also, the user terminal 20 may display biometric information measured by the biometric sensor 40 and display status information regarding the medical liquid injection device 10.

The user terminal 20 refers to a communication terminal usable in a wired/wireless communication environment. For example, the user terminal 20 may include a smartphone, a tablet PC, a PC, a smart TV, a mobile phone, a personal digital assistant (PDA), a laptop computer, a media player, a micro server, a global positioning system (GPS) device, an e-book reader, a digital broadcasting terminal, a navigation device, a kiosk, an MP3 player, a digital camera, a home appliance, a device equipped with a camera, and other mobile or non-mobile computing devices. Also, the user terminal 2 may be a wearable device having a communication function and a data processing function, e.g., a watch, glasses, a hair band, and a ring. However, as described above, any terminal equipped with an application capable of internet communication may be employed without limitation.

The user terminal 20 may be connected one-to-one with a pre-registered controller 30. The user terminal 20 may be connected to the controller 30 through encryption to prevent the controller 30 from being driven and controlled by an external device.

According to an embodiment, the user terminal 20 and the controller 30 may be separated from each other and provided as separate devices. For example, the controller 30 may be provided to a subject equipped with the medical liquid injection device 10, and the user terminal 20 may be provided to the subject or a third person. The user terminal 20 may be driven by a guardian, and thus the safety of the medical liquid injection system 1 may be improved.

According to another embodiment, the user terminal 20 and the controller 30 may be provided as a single device. The controller 30 integrated with the user terminal 20 may communicate with the medical liquid injection device 10 and control injection of a medical liquid.

The controller 30 may perform a function of transmitting and receiving data to and from the medical liquid injection device 10, transmit a control signal related to the injection of a medical liquid like insulin to the medical liquid injection device 10, and receive a control signal related to the measurement of a biometric value like blood glucose from the biometric sensor 40.

For example, the controller 30 may transmit an instruction request to measure the current state of a user to the medical liquid injection device 10 and receive measurement data from the medical liquid injection device 10 in response to the instruction request.

The biometric sensor 40 may perform a function of measuring a user's biometric values like a blood glucose level, a blood pressure, a heart rate, etc. according to purposes. Data measured by the biometric sensor 40 may be transmitted to the controller 30, and an injection cycle and/or an injection amount of a medical liquid may be set based on the measured data. Data measured by the biometric sensor 40 may be transmitted to the user terminal 20 and displayed thereon.

For example, the biometric sensor 40 may be a sensor that measures a blood glucose level of a target object. The biometric sensor 40 may be a continuous glucose monitoring (CGM) sensor. A CGM sensor may be attached to a target object to continuously monitor a blood glucose level of the target object.

The user terminal 20, the controller 30, and the medical liquid injection device 10 may perform communication with one another by using a network. For example, the network is a comprehensive data communication network that includes a Local Area Network (LAN), a Wide Area Network (WAN), a Value Added Network (VAN), a mobile radio communication network, a satellite communication network, and mutual combinations thereof and allows network constituent entities to communicate smoothly with one another and may include wired Internet, wireless Internet, and a mobile wireless communication network. Also, wireless communication may include, for example, wireless LAN (Wi-Fi), Bluetooth, Bluetooth low energy (Bluetooth low energy), Zigbee, WFD (Wi-Fi Direct), UWB (ultra wideband), infrared communication (IrDA, infrared Data Association), NFC (Near Field Communication), and 5G, but the present disclosure is not limited thereto.

Figure 2:
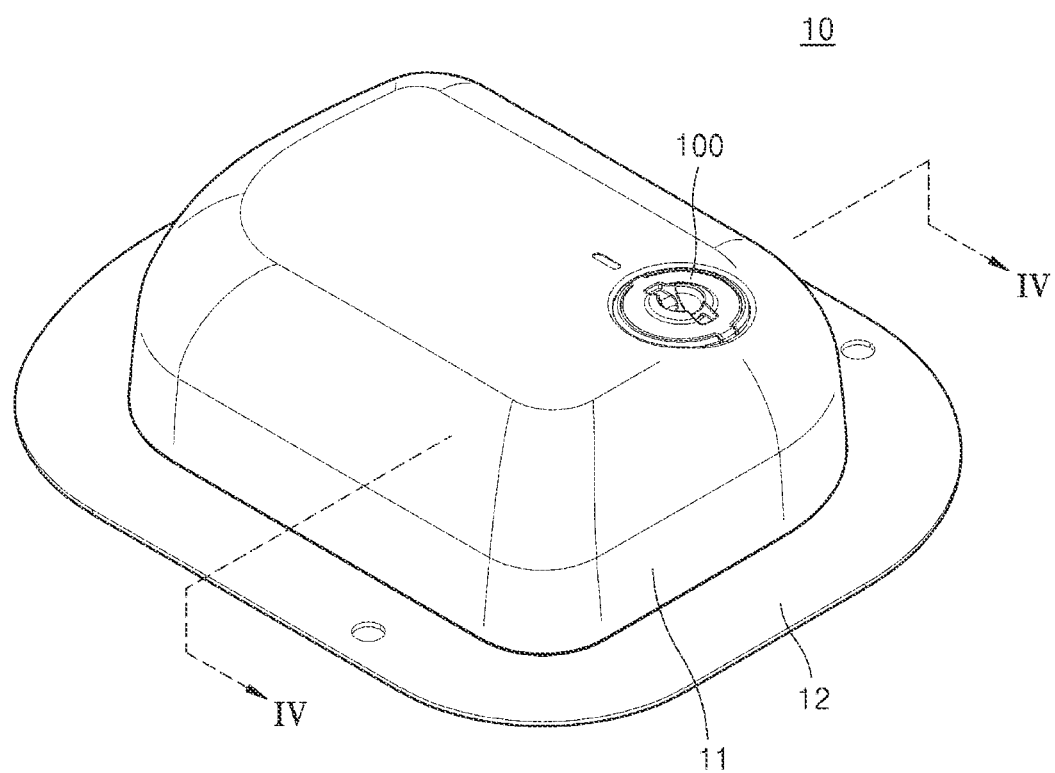
FIG. 2 is a perspective view showing a medical liquid injection device according to an embodiment of the present disclosure.
Figure 3:
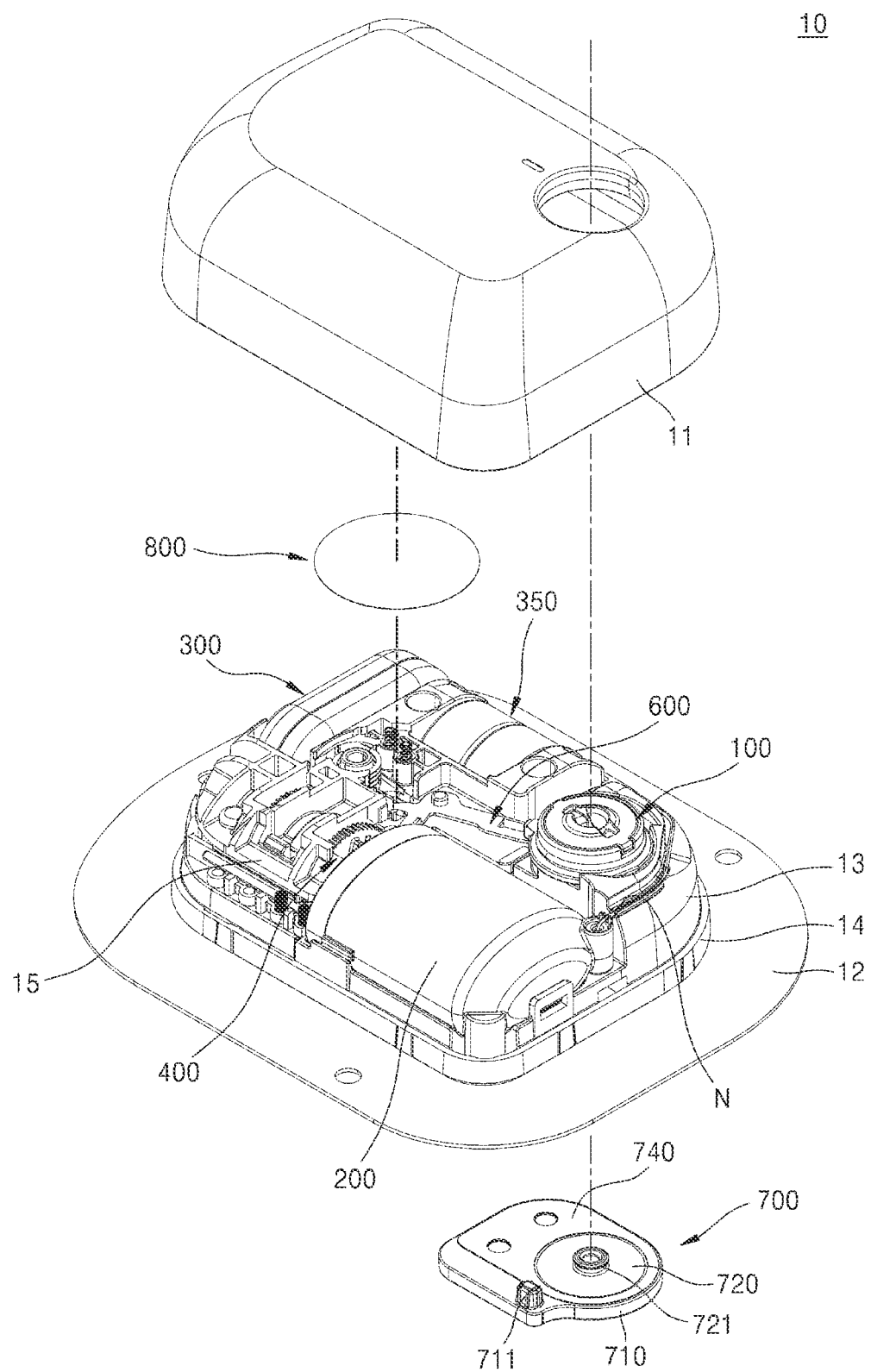
FIG. 3 is an exploded perspective view of the medical liquid injection device of FIG. 2.
Figure 4:
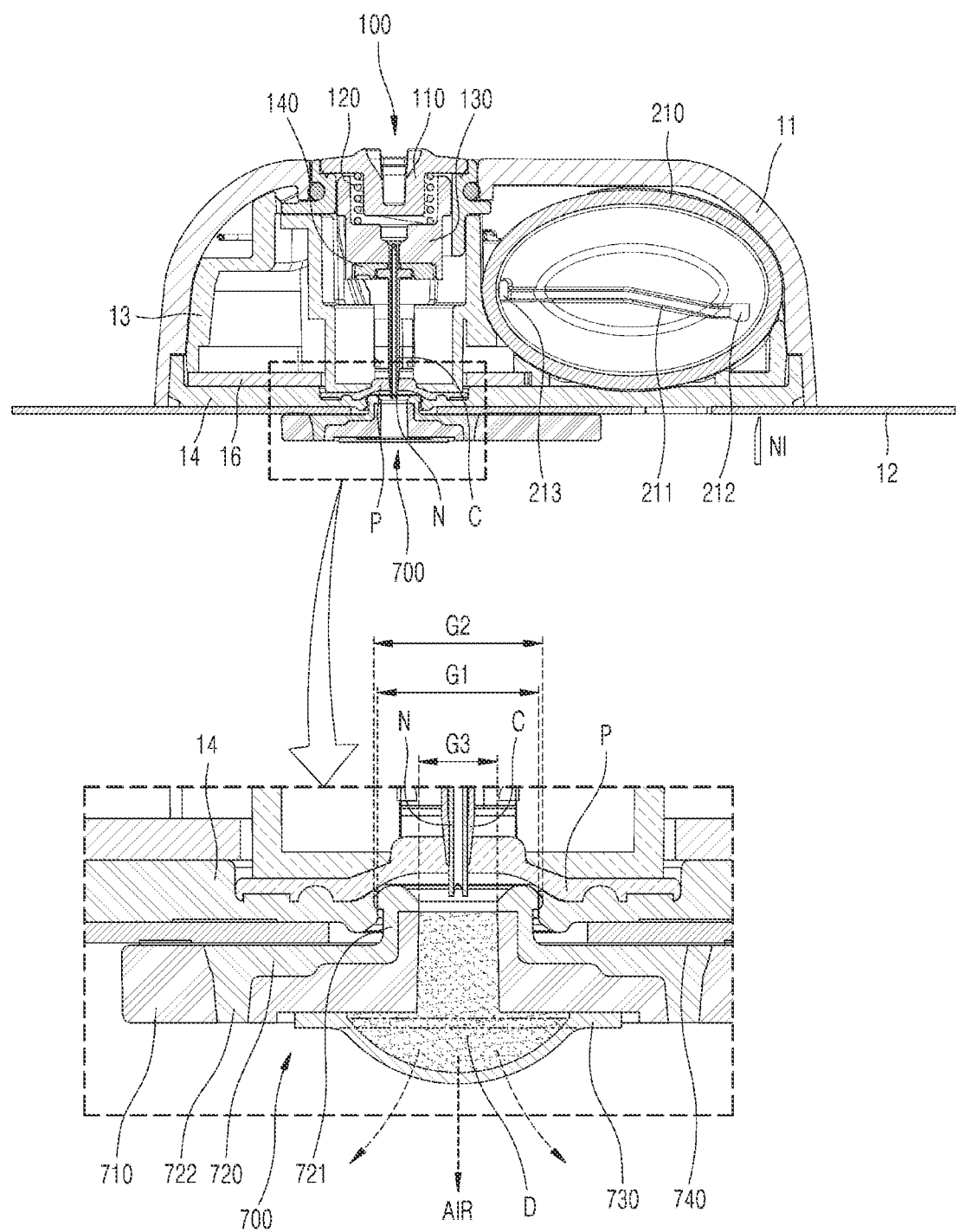
FIG. 4 is a cross-sectional view taken along a line IV-IV of FIG. 2.

FIG. 2 is a perspective view of a medical liquid injection device 10 according to an embodiment of the present disclosure, FIG. 3 is an exploded perspective view of the medical liquid injection device 10 of FIG. 2, and FIG. 4 is a cross-sectional view taken along a line IV-IV of FIG. 2.

Referring to FIGS. 2 to 4, the medical liquid injection device 10 may be attached to a user subject to medical liquid injection and may inject a medical liquid stored therein to the user in a set amount.

The medical liquid injection device 10 may be used for various purposes depending on the type of medical liquid to be injected. For example, the medical liquid may include an insulin-based medical liquid for diabetic patients, other medical liquids for pancreas, cardiac medical liquids, and other various types of medical liquids.

The medical liquid injection device 10 according to an embodiment may include a housing 11 covering the outer portion and an attachment portion 12 positioned adjacent to the skin of a user. The medical liquid injection device 10 includes a plurality of parts arranged in an inner space between the housing 11 and the attachment portion 12. A separate bonding means may be further provided between the attachment portion 12 and the skin of a user, and the medical liquid injection device 10 may be fixed to the skin by the bonding means.

The medical liquid injection device 10 may include a needle assembly 100, a reservoir unit 200, a driving module 300, a battery 350, a driving unit 400, a clutch unit 500, a trigger member 600, a needle cover assembly 700, an alarm unit 800, and a plurality of sensor units.

In the medical liquid injection device 10, a base body may form a frame in which at least one body supports internal components. The base body may include a first body 13, a second body 14, and a third body 15 according to arrangements.

The first body 13 is disposed below the housing 11, and the needle assembly 100, the reservoir unit 200, the driving module 300, the battery 350, etc. may be supported in respective openings or grooves. The second body 14 is disposed below the first body 13 and may be connected to the attachment portion 12. The second body 14 may cover the lower portion of the medical liquid injection device 10. The third body 15 is disposed above the first body 13 and may support the reservoir unit 200, the driving module 300, the battery 350, the driving unit 400, etc. in respective openings or grooves. In the drawings, the first body 13, the second body 14 and the third body 15 are shown. However, the present disclosure is not limited thereto, and there may be a single integrated body or a plurality of bodies.

A control module 16 may be disposed inside the medical liquid injection device 10. The control module 16, which is a circuit board, is disposed below the second body 14 and may control the overall driving of the medical liquid injection device 10. The control module 16 may electrically contact the driving module 300, the battery 350, the alarm unit 800, and the plurality of sensor units and control drivings thereof.

The needle assembly 100 may be attached to the first body 13. In the needle assembly 100, a needle N and/or a cannula C may move in an axial direction by rotation of a sleeve 110. The needle assembly 100 may include the sleeve 110, an elastic member 120, a first holder 130, a second holder 140, the needle N, the cannula C, and a patch P.

The sleeve 110 forms the outer portion of the needle assembly 100 and may be rotated around the central axis in the lengthwise direction. The elastic member 120 is disposed inside the sleeve 110, and thus the sleeve 110 may receive an expansion force from the elastic member 120.

The elastic member 120 may be disposed between the sleeve 110 and the first holder 130. When the elastic member 120 expands, the first holder 130 may be moved downward. Also, when the first holder 130 moves upward, the elastic member 120 may be compressed.

The first holder 130 may support the needle N. Since the needle N is inserted and fixed to one side of the first holder 130, when the first holder 130 moves in the axial direction, the needle N also moves. The first holder 130 is disposed in the inner space of the sleeve 110, while the elastic member 120 is disposed above the first holder 130.

The second holder 140 is disposed to face one side of the first holder 130 and may support the cannula C. The second holder 140 includes a flexible material, and thus the second holder 140 may be instantly deformed in shape when an external force is applied thereto. Alternatively, the second holder 140 may include a rigid material, and thus the second holder 140 may be moved by a force applied by the first holder 130.

Since the needle N is fixed to the first holder 130, the needle N may be inserted into or released from the cannula C by the axial movement of the first holder 130. A first end of the needle N may be connected to a reservoir 210, and thus a medical liquid may be delivered through the needle N. Meanwhile, a second end of the needle N may be inserted into the cannula C, and thus the needle N may move along the cannula C.

Since the cannula C is fixed to the second holder 140, the cannula C may be inserted into the skin of a user by the axial movement of the second holder 140. Since the cannula C has a conduit shape capable of accommodating the needle N, a medical liquid discharged from the needle N may be injected into a user.

The patch P is supported on one side of the medical liquid injection device 10 and may fix the position of the cannula C. Since an end of the cannula C is supported by the patch P, the separation of the cannula C from during storage or movement may be prevented.

An end of the needle N and/or an end of the cannula C is inserted into the patch P. Before a medical liquid is injected into a user, that is, before the needle N and the cannula C are inserted into the user, the end of the needle N and/or the end of the cannula C may be supported by the patch P and positions thereof may be set. When a medical liquid is injected into the reservoir 210, the positions of the needle N and the cannula C are fixed, and thus gas remaining in the reservoir 210 may be stably discharged.

The cannula C may continue to be inserted into the skin of a user, but the needle N rises and is separated therefrom. However, the cannula C and the needle N form a path through which a fluid is moved, and thus a medical liquid injected from the reservoir 210 may be injected into the user through the needle N and the cannula C.

In the medical liquid injection device 10, a user may simply rotate the needle assembly 100 to insert the cannula C into a target object and initiate medical liquid injection. In the medical liquid injection device 10, as a user first rotates the sleeve 110, the cannula C may be inserted into a target object, and a knob (not shown) of the needle assembly 100 may press and drive the trigger member 600. Thereafter, the driving module 300 is driven, and thus a medical liquid of a fixed amount may be discharged from the reservoir 210. Therefore, the user may conveniently and stably use the medical liquid injection device 10.

Figure 5:
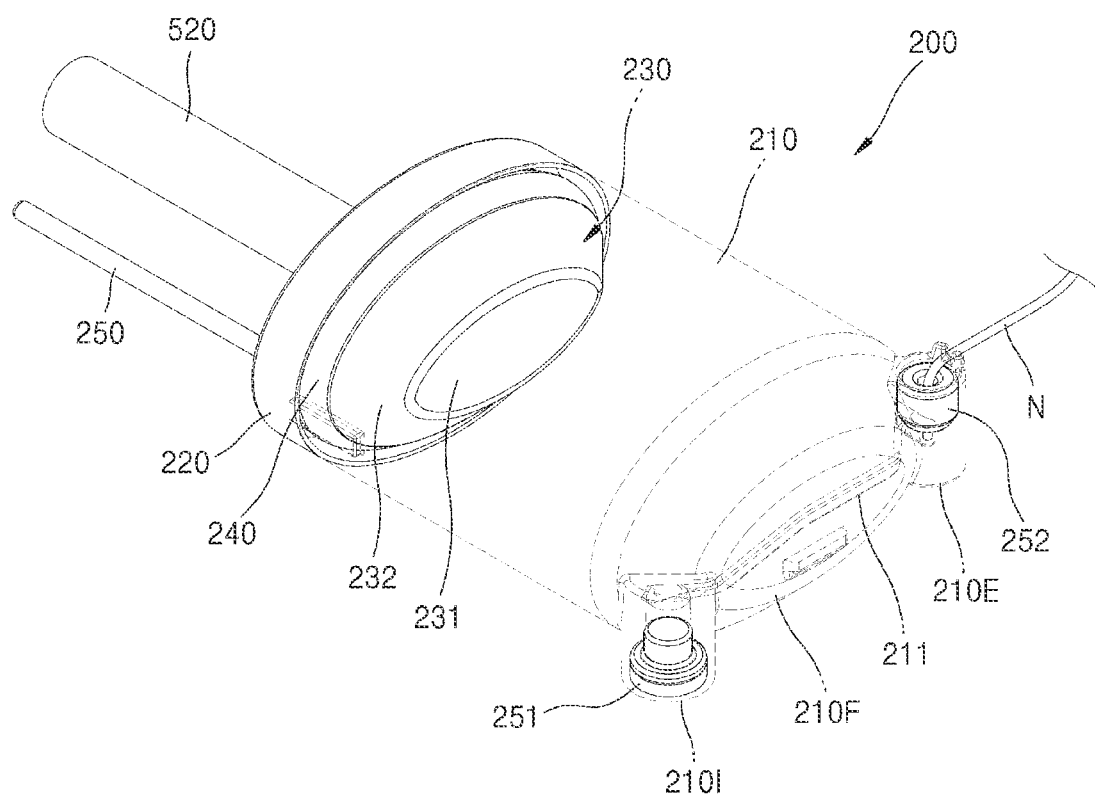
FIG. 5 is a diagram showing a reservoir unit of FIG. 2.
Figure 6A:
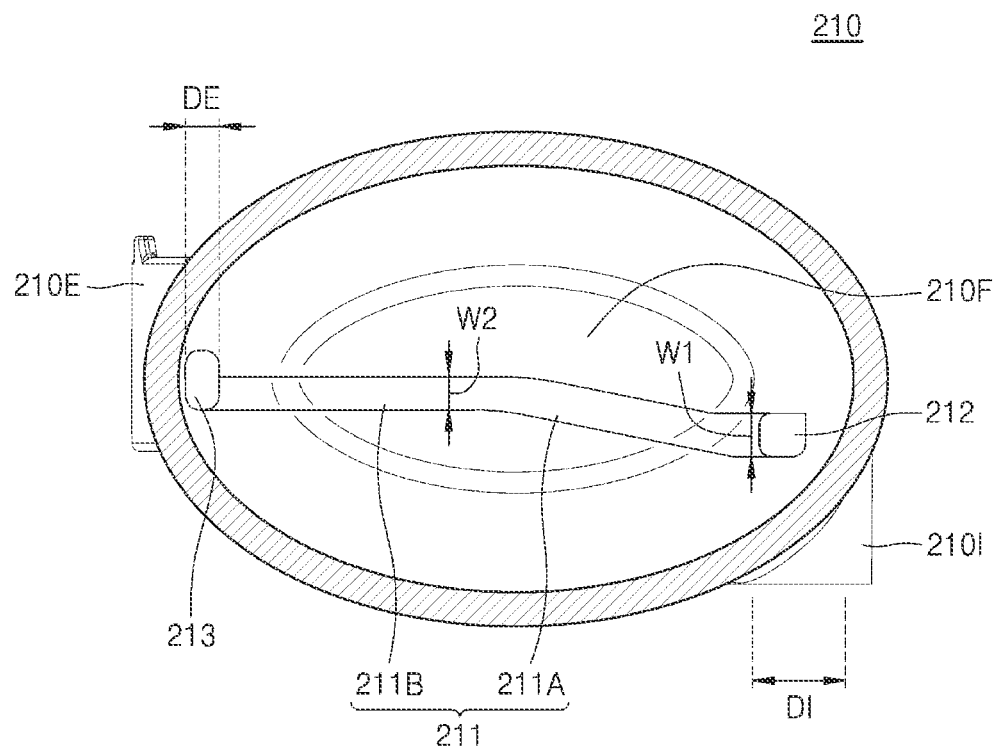
FIG. 6A is a cross-sectional view of the reservoir unit of FIG. 5, and FIGS. 6B and 6C are diagrams showing modified examples of the reservoir unit.
Figure 6B:
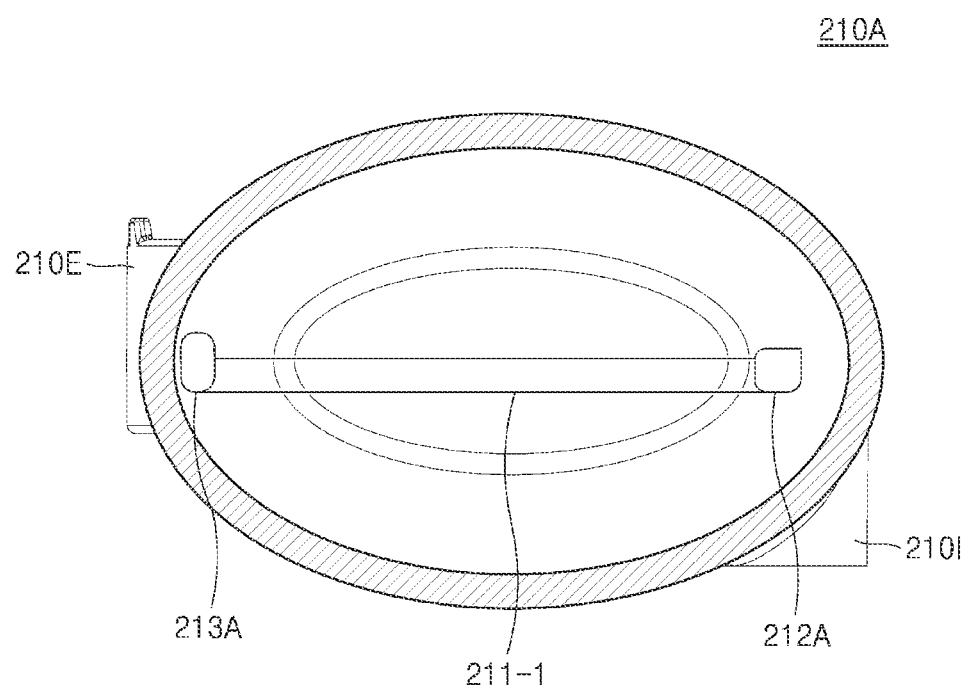
Figure 6C:
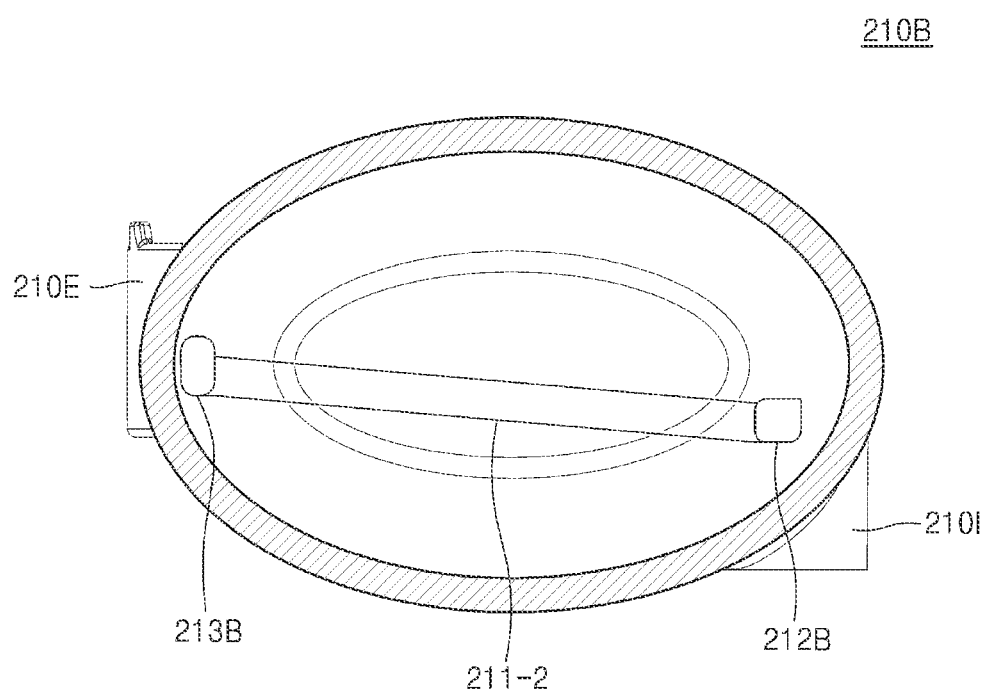

FIG. 5 is a diagram showing the reservoir unit 200 of FIG. 2, FIG. 6A is a cross-sectional view of the reservoir unit 200 of FIG. 5, and FIGS. 6B and 6C are diagrams showing modified examples of the reservoir unit 200.

Referring to FIGS. 5 and 6A, the reservoir unit 200 is attached to the first body 13 and the third body 15 and is connected to the needle assembly 100. A medical liquid D is stored in the inner space of the reservoir unit 200, and the medical liquid D of a fixed amount may be moved to the needle N according to the movement of a plunger 230. The reservoir unit 200 may include the reservoir 210, a cap cover 220, the plunger 230, and a sealing ring 240. Also, the reservoir unit 200 may include a connecting member 520.

The reservoir 210 may extend to a pre-set length in the lengthwise direction and store a medical liquid in the inner space thereof. A medical liquid may be discharged from the reservoir 210 to the needle N by the movement of the plunger 230. The cap cover 220 is attached to an end of the reservoir 210, and a rod 410 and/or a connecting member 520 may move through an opening (not shown) disposed in the cap cover 220.

The reservoir 210 may have an inlet end 210I and an outlet end 210E. A medical liquid is injected through the inlet end 210I, the needle N is installed at the outlet end 210E, and the medical liquid may be discharged through the needle N.

The inlet end 210I is connected to the lower portion of the medical liquid injection device 10, and a medical liquid may be injected by a separate medical liquid injector NI. A first sealing member 260 is disposed at the inlet end 210I, and the first sealing member 260 may prevent leakage of a medical liquid. The inlet end 210I may have a first connection opening 212 connected to a guide groove 211.

The outlet end 210E is disposed to be apart from the inlet end 210I and is connected to the needle N, and thus a medical liquid may be discharged therethrough. A second sealing member 252 is disposed at the outlet end 210E, and the needle N may be fixed to the second sealing member 252. The outlet end 210E may have a second connection opening 213 connected to the guide groove 211.

A first diameter DI of the inlet end 210I may be set to be greater than a second diameter DE of the outlet end 210E. Since a needle of the medical liquid injector NI is inserted into the inlet end 210I, the inlet end 210I may have a sufficient opening area into which the needle may be inserted.

The guide groove 211 may be disposed on an inner surface of the reservoir 210. At least a portion of the guide groove 211 may extend to interconnect the inlet end 210I and the outlet end 210E.

The guide groove 211 may form a path for guiding gas remaining in the inner space of the reservoir 210 to the needle assembly 100. More specifically, inside the reservoir 210, there is a gas (air) remaining during an assembly process or a manufacturing process in a gap between the front end of the reservoir 210 and the plunger 230. When a medical liquid is injected into the reservoir 210 through the external medical liquid injector NI, the gas may be discharged through the needle N along the guide groove 211.

According to an embodiment, the guide groove 211 may extend to interconnect the inlet end 210I and the outlet end 210E (refer to FIG. 6A).

The guide groove 211 may include a first guide groove 211A and a second guide groove 211B connected to each other. The first guide groove 211A may be connected to the inlet end 210I, and the second guide groove 211B may be connected to the outlet end 210E. When the inlet end 210I and the outlet end 210E are arranged at different heights, at least one of the first guide groove 211A and the second guide groove 211B may be inclined.

For example, referring to the drawings, the first guide groove 211A may extend from the first connection opening 212 in an upward direction. The second guide groove 211B is connected to the first guide groove 211A and may be connected to the second connection opening 213. At this time, the second guide groove 211B may extend in a horizontal direction.

The first guide groove 211A and the second guide groove 211B may each have a certain width. A first width W1 of a portion of the first guide groove 211A adjacent to the inlet end 210I may be set to be greater than that of other portions of the first guide groove 211A. A portion of the first guide groove 211A and the second guide groove 211B may each have a second width W2, and a portion of the first guide groove 211A adjacent to the first connection opening 212 may have the first width W1 greater than the second width W2. Since the first guide groove 211A is disposed to have an expanded portion having the first width W1, a medical liquid injected through the inlet end 210I may be guided to the reservoir 210, and, when a medical liquid is injected through the inlet end 210I, the movement of a gas from a portion corresponding to the first width W1 to a portion corresponding to the second width W2 is guided, and thus the air may be easily discharged.

The guide groove 211 may have any of various cross-sectional shapes. The guide groove 211 may be formed to have a polygonal cross-sectional shape or may be formed to have at least a portion with a curved surface.

The guide groove 211 may be disposed on an inner surface of the front portion of the reservoir 210. The front portion of the reservoir 210 may have an inclined portion and a flat portion in correspondence to the shape of the plunger 230. The guide groove 211 may extend to the first connection opening 212 and the second connection opening 213 along the inclined portion and the flat portion.

According to another embodiment, a guide groove may be disposed between the inlet end 210I and the outlet end 210E, may be connected to at least one of the inlet end 210I and the outlet end 210E, and may not be connected to the other one of the inlet end 210I and the outlet end 210E. For example, a first end of the guide groove may be connected to the inlet end 210I, and a second end of the guide groove may be spaced apart from the outlet end 210E. A first end of the guide groove 211 may be connected to the outlet end 210E, and a second end of the guide groove 211 may be spaced apart from the inlet end 210I.

According to another embodiment, a guide groove may be disposed between the inlet end 210I and the outlet end to be spaced apart from both the inlet end 210I and the outlet end 210E. For example, the guide groove 211 may not be connected to the inlet end 210I and the outlet end 210E and may be disposed between the inlet end 210I and the outlet end 210E.

According to another embodiment, a plurality of guide grooves may be provided and arranged between the inlet end 210I and the outlet end 210E. For example, a plurality of divided guide grooves may be arranged in a space between the inlet end 210I and the outlet end 210E.

Referring to FIG. 6B, a reservoir 210A may include the inlet end 210I and the outlet end 210E and may have a guide groove 211-1 extending to interconnect the inlet end 210I and the outlet end 210E.

The guide groove 211-1 may interconnect a first connection opening 212A and a second connection opening 213A. Since the first connection opening 212A and the second connection opening 213A are arranged at the same height, the guide groove 211-1 may extend horizontally.

Referring to FIG. 6C, a reservoir 210B may include the inlet end 210I and the outlet end 210E and may have a guide groove 211-2 extending to interconnect the inlet end 210I and the outlet end 210E.

The guide groove 211-2 may interconnect a first connection opening 212B and a second connection opening 213B. Since the first connection opening 212B and the second connection opening 213B are arranged at different heights, the guide groove 211-2 may be inclined.

The plunger 230 is disposed inside the reservoir 210 and may move linearly by being driven by the driving module 300 and the driving unit 400. As the plunger 230 advances, a medical liquid may be discharged from the inner space of the reservoir 210 to the needle N.

The plunger 230 may have an end 231 and an inclined surface 232. The end 231 may move toward the front of the reservoir 210 to move a medical liquid. The inclined surface 232 may closely contact the inclined portion of the reservoir 210.

The plunger 230 may include the connecting member 520 extending rearward. The connecting member 520 may be installed on the plunger 230 and move linearly along with the linear movement of the plunger 230.

The connecting member 520 includes a material having electrical conductivity and may have a shaft-like shape. As the connecting member 520 moves and contacts a first sensor unit 910A, the storage amount of a medical liquid may be measured or the medical liquid injection device 10 may be started to be driven.

The connecting member 520 may be connected to the rear end of the plunger 230 and move together as the plunger 230 moves. Although it is illustrated in the drawings that the connecting member 520 has a shaft-like shape, the present disclosure is not limited thereto, and the connecting member 520 may have various shapes for generating electrical signals by contacting the first sensor unit 910A.

When a medical liquid is stored in the reservoir 210 and the plunger 230 retracts, the connecting member 520 may retract together with the plunger 230. Also, when the plunger 230 moves forward to discharge the medical liquid from the reservoir 210 to the needle N, the connecting member 520 may move forward together with the plunger 230.

The sealing ring 240 may be provided at a portion of the plunger 230 contacting the reservoir 210, thereby preventing leakage of a medical liquid during the movement of the plunger 230.

Figure 7:
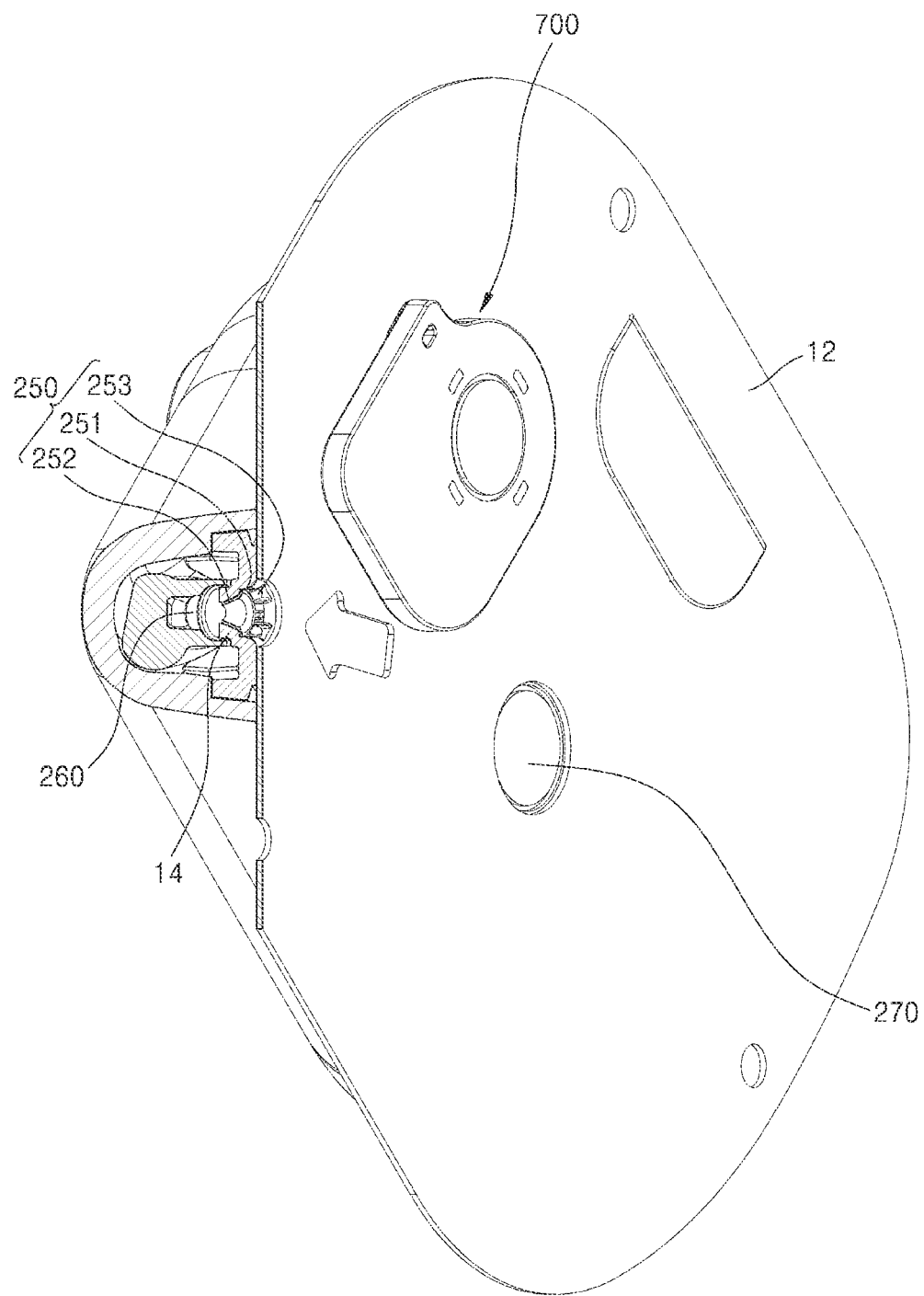
FIG. 7 is a perspective view showing the cross-section of a portion of the medical liquid injection device of FIG. 2.
Figure 8:
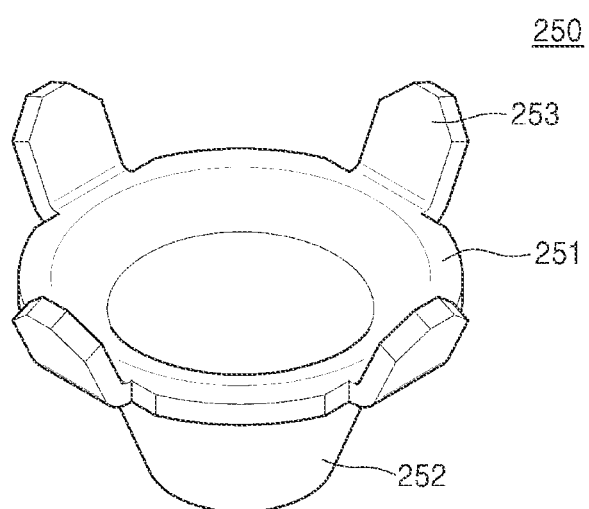
FIG. 8 is a perspective view of a guide cap of FIG. 7.
Figure 9:
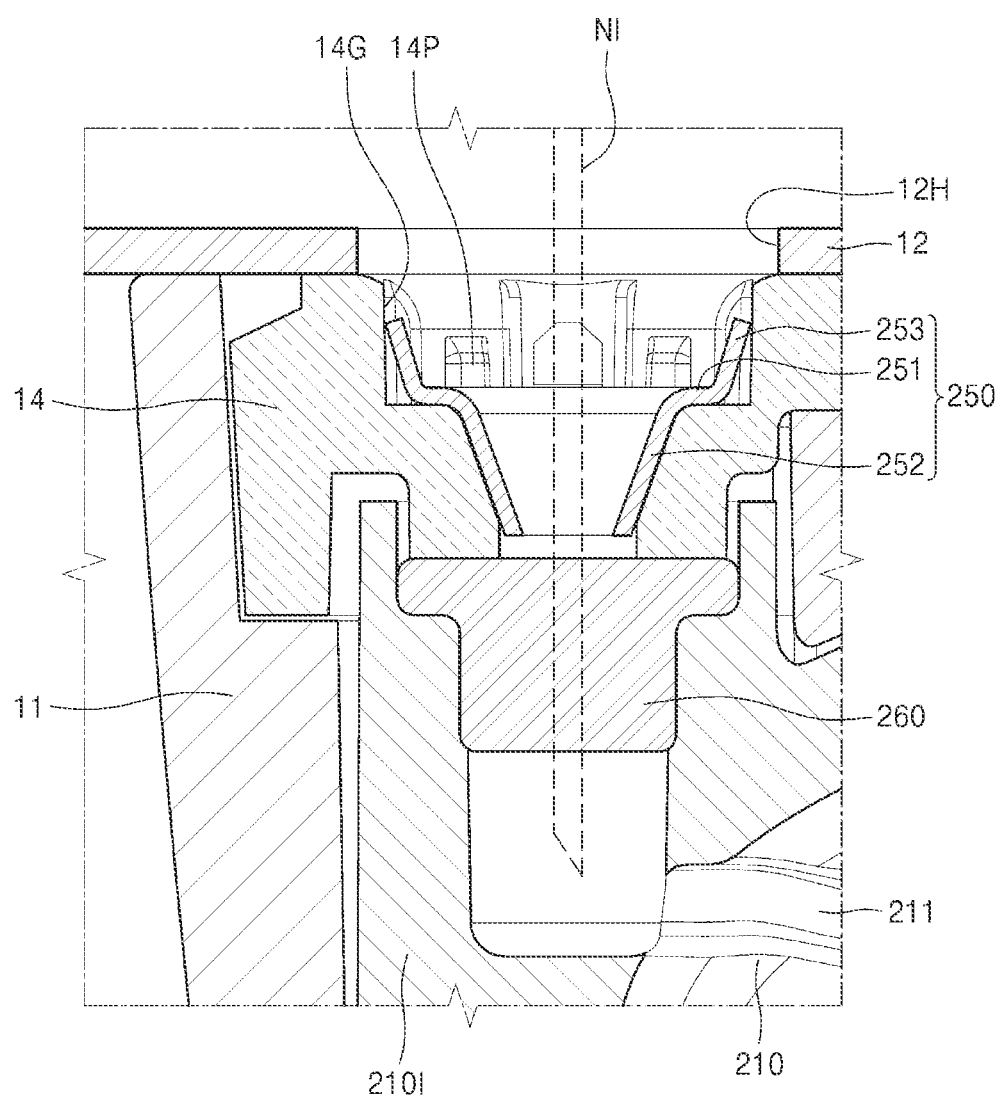
FIG. 9 is a cross-sectional view of a portion of the medical liquid injection device of FIG. 2.

FIG. 7 is a perspective view of a cross-section of a portion of the medical liquid injection device 10 of FIG. 2, FIG. 8 is a perspective view of a guide cap 250 of FIG. 7, and FIG. 9 is a partial cross-sectional view of the medical liquid injection device 10 of FIG. 2.

Referring to FIGS. 7 to 9, the guide cap 250 may be disposed to face a sealing member 260 and may be attached to a base body. The guide cap 250 is disposed adjacent to the sealing member 260 and may guide insertion and movement of an injection needle of the medical liquid injector NI.

The guide cap 250 may be inserted into the second body 14 and disposed below an opening 12H of the attachment portion 12. In detail, the sealing member 260 is attached between the second body 14 and the reservoir 210, and the guide cap 250 faces the sealing member 260 and is installed in an opening of the second body 14. When a user inserts the injection needle of the medical liquid injector NI, the injection needle passes through the guide cap 250 and penetrates through the sealing member 260.

The guide cap 250 may include a flange 251, an inclined end 252, and a wing piece 253.

The flange 251 may be attached to a seating end of the base body. The second body 14 has a flat seating end and is inserted such that the flange 251 contacts the seating end.

The inclined end 252 extends from the flange 251 and has a slope, such that an open cross-sectional area thereof is reduced. The inclined end 252 may extend from the flange 251 to the sealing member 260, such that the cross-sectional area thereof is reduced. Therefore, an opening area thereof at the flange 251 is larger than an opening area thereof at the end of the inclined end 252.

The inclined end 252 may guide the injection needle of the medical liquid injector NI to be inserted into a pre-set position. When a user inserts the medical liquid injector NI, the injection needle of the medical liquid injector NI may be inserted into a certain position by the inclined end 252.

The wing piece 253 extends outward from the flange 251 and may be supported by the base body. A plurality of wing pieces 253 may be arranged outside the flange 251 to be apart from one another. Since the wing pieces 253 are arranged apart from one another, the wing pieces 253 may be inserted into the second body 14 by applying force by using an external device (not shown).

In the second body 14, insertion grooves 14G into which the wing pieces 253 are inserted may be spaced apart from one another, and protrusions 14P supporting the flange 251 may be arranged between the insertion grooves 14G. The wing pieces 253 may be inserted into the insertion grooves 14G of the second body 14, and thus the guide cap 250 may be fixed to the second body 14. The wing pieces 253 may be supported on the sidewalls of the insertion grooves 14G by elasticity and rigidity. Also, the upper end of the flange 251 may be supported by the protrusions 14P, and thus the position of the flange 251 may be set. The fixing structure including the wing pieces 253 and the protrusions 14P may stably couple the guide cap 250 to the second body 14.

The guide cap 250 may have a curved surface in an area where the flange 251 and the inclined end 252 are connected to each other. Since the flange 251 and the inclined end 252 are smoothly connected to each other, the injection needle of the medical liquid injector NI may be smoothly inserted into the sealing member 260 along the inclined end 252.

The guide cap 250 may include a material having a certain rigidity. For example, the guide cap 250 may include a metal material, and, for example, the guide cap 250 may include a SUS-based material.

The rigidity of the guide cap 250 may be set to be greater than the rigidity of the injection needle of the medical liquid injector NI. The guide cap 250 may have rigidity not to be scratched by injection needles of the medical liquid injector NI. In other words, since the rigidity of the guide cap 250 is greater than the rigidity of the injection needle of the medical liquid injector NI, even when the guide cap 250 is scratched by the injection needle of the medical liquid injector NI during insertion of the medical liquid injector NI, foreign substances like debris are not introduced into the reservoir 210.

The guide cap 250 may be inserted to a pre-set depth from the surface of the base body. The guide cap 250 is disposed below the surface of the second body 14 and mounted such that the same enters via the bottom surface of the medical liquid injection device 10. Since the guide cap 250 does not protrude to the outside, it is possible to prevent foreign substances from entering into the reservoir 210.

The guide cap 250 is attached to an open portion of the medical liquid injection device 10, such that a user may see the guide cap 250 from the outside. Since a user may recognize the position of the guide cap 250 through openings of the attachment portion 12 and the second body 14, the injection needle of the medical liquid injector NI may be easily and accurately aligned to the center of the guide cap 250 and inserted into the sealing member 260.

The sealing member 260 includes a first part 261 having a first width, and the first part 261 is inserted into the inlet end 210I of the reservoir 210. The sealing member 260 includes a second part 262 having a second width greater than the first width, and the second part 262 extends from an end of the first part 261. Since the upper portion of the second part 262 is supported by the second body 14 and the lower portion is supported by the inlet end 210I, the position of the sealing member 260 is firmly fixed. In other words, since the sealing member 260 is supported by the second part 262 at the inlet end 210I of the reservoir 210, leakage of a medical liquid from the reservoir 210 may be completely prevented.

Figure 10:
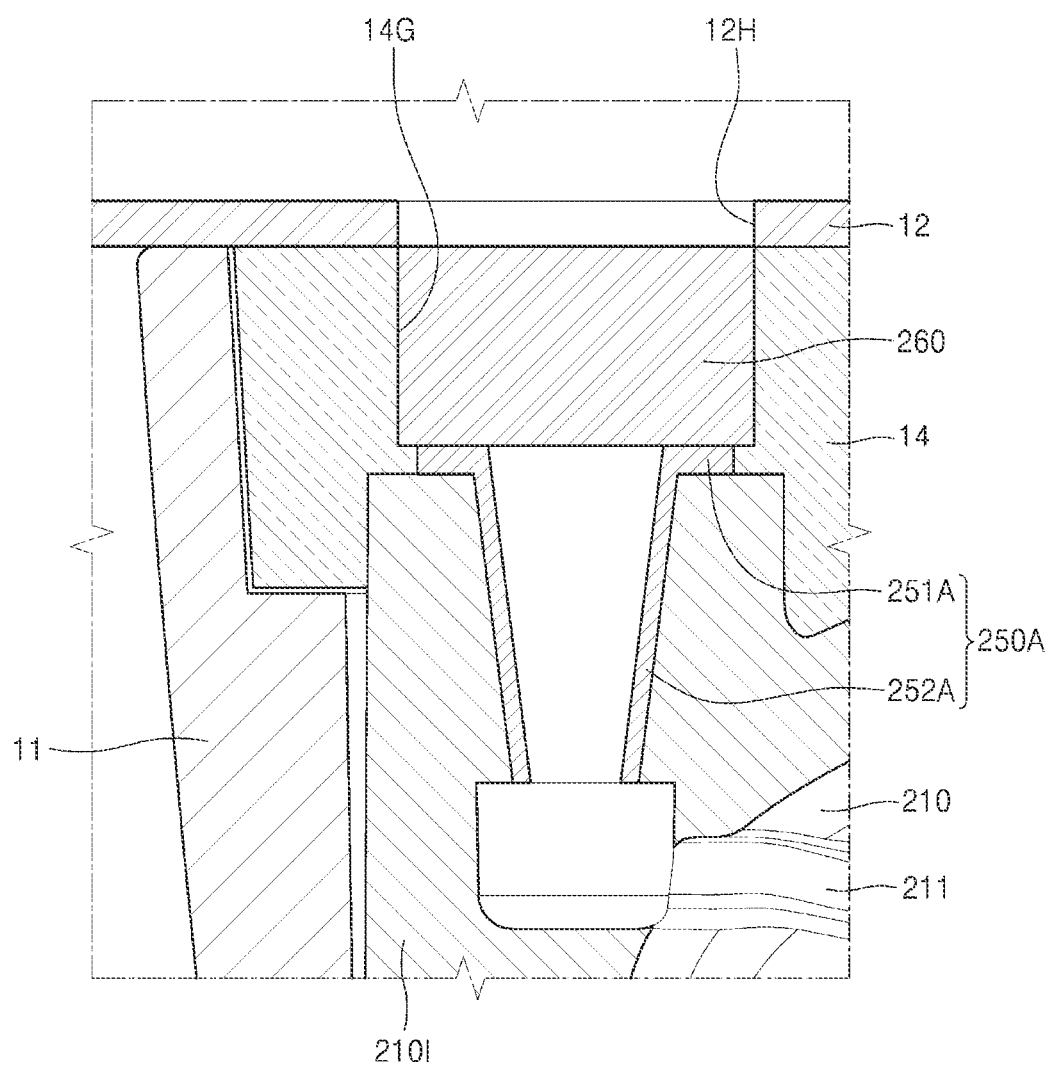
FIG. 10 is a partial cross-sectional view of a medical liquid injection device according to a modified example of FIG. 7.

FIG. 10 is a partial cross-sectional view of a medical liquid injection device according to a modified example of FIG. 7.

Referring to FIG. 10, in a medical liquid injection device, a guide cap 250A may be disposed at the inlet end 210I of the reservoir 210, and the sealing member 260 may be disposed above the guide cap 250A.

The guide cap 250A may be disposed between the inlet end 210I of the reservoir 210 and the sealing member 260 to guide the movement of the injection needle of the medical liquid injector NI and the movement of a medical liquid.

The guide cap 250A may have a flange 251A and an inclined end 252A. The flange 251A is attached to the outside of the inlet end 210I, and the inclined end 252A may be inserted inside the inlet end 210I. The flange 251A may fix the position of the guide cap 250A and may be supported by the sealing member 260.

A medical liquid is introduced into the inclined end 252A at the inlet, and the outlet of the inclined end 252A is connected to the reservoir 210. Since the inclined end 252A has a certain inclination, the inclined end 252A may guide the movement of a medical liquid.

The rigidity of the inclined end 252A may be set to be greater than the rigidity of the injection needle of the medical liquid injector NI. Even when the injection needle of the medical liquid injector NI scratches the surface of the inclined end 252A, foreign substances are not introduced into the reservoir 210.

The sealing member 260 is disposed on top of the guide cap 250A to prevent leakage of a medical liquid from the reservoir 210. Also, to inject a medical liquid into the reservoir 210, an injection needle may be inserted into the sealing member 260.

The sealing member 260 may be set to be transparent or semi-transparent, such that the guide cap 250A may be seen therethrough. Since a medical liquid is safely stored in the reservoir 210 when the injection needle is inserted through the center of the guide cap 250A, it is important for a user to insert the injection needle at the center of the guide cap 250A. Since a user may see the guide cap 250A through the sealing member 260, the injection needle may be accurately inserted through the guide cap 250A.

Figure 11:
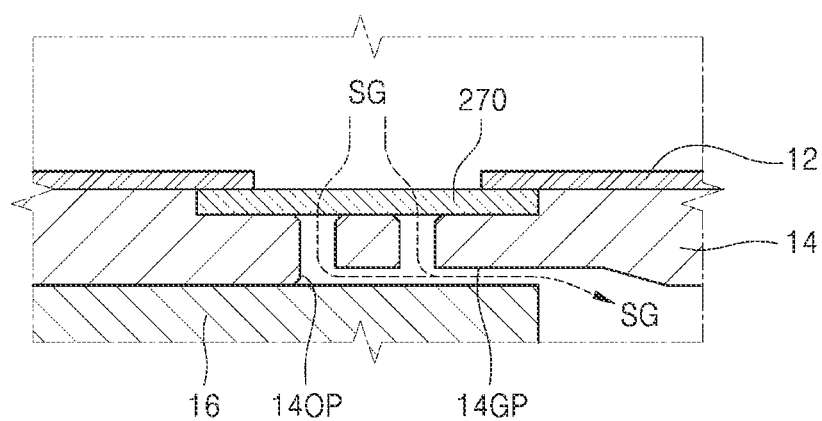
FIG. 11 is a cross-sectional view showing the coupling relationship of a sterilization cover of FIG. 7.

FIG. 11 is a cross-sectional view showing the coupling relationship of a sterilization cover 270 of FIG. 7.

Referring to FIG. 11, the sterilization cover 270 is disposed at the bottom of the medical liquid injection device 10, and sterilization gas may be injected.

Since the medical liquid injection device 10 is a device attached to the human body, each component needs to be disinfected before being attached to a user. After components of the medical liquid injection device 10 are assembled, a sterilization gas SG may be injected through the sterilization cover 270 to sterilize internal components of the medical liquid injection device 10.

Gases like a sterilization gas pass through the sterilization cover 270, but liquids like a medical liquid do not pass through the sterilization cover 270. Therefore, when the sterilization gas SG is injected through the sterilization cover 270, a sterilization gas passes through the second body 14 and is introduced into the inner space of the medical liquid injection device 10. The sterilization gas SG may improve the safety of the medical liquid injection device 10 by sterilizing the internal components thereof.

An opening 14OP is formed in the second body 14 at a position facing the sterilization cover 270, and thus the sterilization gas may move into the inner space of the second body 14.

A path through which the sterilization gas SG may move may be set inside the second body 14. A gap type or a groove type moving path 14GP may be formed between the second body 14 and the control module 16, and thus the sterilization gas SG passed through the opening 14OP may move into the second body 14.

In the medical liquid injection device 10 according to an embodiment of the present disclosure, a path through which the sterilization gas SG moves is set for disinfection, and thus the safety of the medical liquid injection device 10 may be improved.

Referring back to FIG. 3, the driving module 300 may generate driving force and transmit the driving force to the driving unit 400. The driving force transmitted by the driving unit 400 linearly moves the plunger 230 inside the reservoir 210 to discharge a medical liquid.

When driving units 400 are engaged with each other by the clutch unit 500, the driving module 300 may rotate drive wheels 420 of the driving units 400, and the rod 410 may linearly move due to the rotation of the drive wheels 420, and thus the plunger 230 may move. When the plunger 230 moves, the connecting member 520 may also linearly move.

All kinds of devices with medical liquid suction power and medical liquid discharge power by electricity may be used as the driving module 300. For example, all kinds of pumps such as mechanical displacement type micropumps and electromagnetic motion type micropumps may be used. The mechanical displacement micro-pump is a pump that uses the motion of a solid like a gear or a diagram or a fluid to generate a pressure difference to induce a flow of a fluid and may include a diaphragm displacement pump, a fluid displacement pump, a rotary pump, etc. The electromagnetic motion type micropump is a pump that directly uses electrical or magnetic energy to move a fluid, and includes an electro hydrodynamic pump (EHD), an electro osmotic pump, a magneto hydrodynamic pump, an electro wetting pump, and the like.

The battery 350 may supply electricity to the medical liquid injection device 10 to activate components thereof. Although a pair of batteries 350 are shown in the drawings, the present disclosure is not limited thereto, and the number of the batteries 350 may be variously set according to the capacity, the use range, the use time, etc. of the medical liquid injection device 10.

The battery 350 is disposed adjacent to the driving unit 400 and may supply electricity to the driving unit 400. Also, the battery 350 is connected to the control module 16, and, based on an electrical signal measured by a sensor unit, the sensor unit may measure data regarding the number of rotations or the rotational speed of the driving unit 400, an amount of medical liquid stored in the reservoir 210, an amount of a medical liquid injected into a user, etc.

Figure 12:
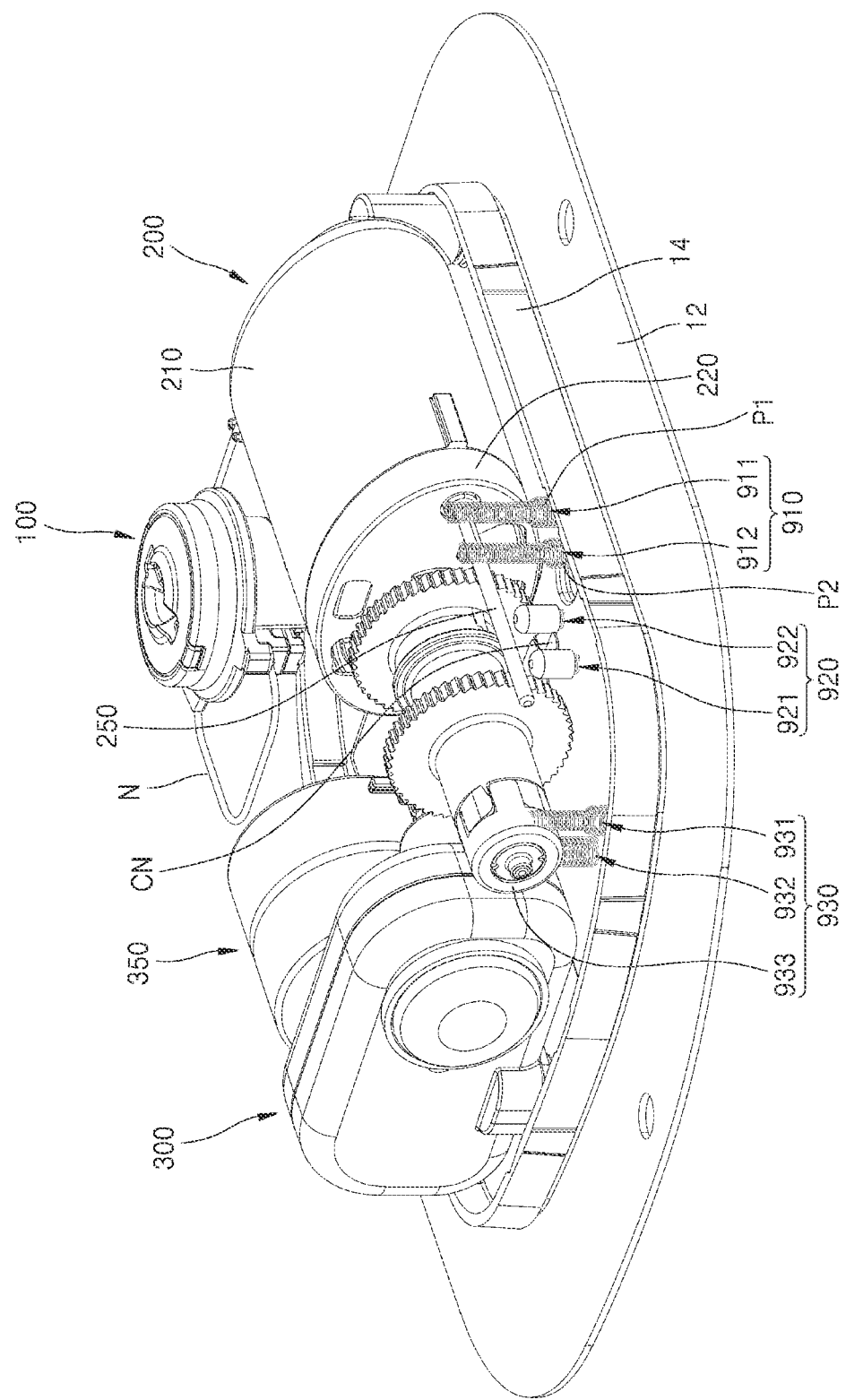
FIG. 12 is a perspective view of some of the components of FIG. 2.

FIG. 12 is a perspective view of some of components of FIG. 2, and FIGS. 13 to 16 are cross-sectional views showing operations for injecting a medical liquid into a reservoir, storing the medical liquid, and discharging the medical liquid through a needle.

Referring to FIGS. 12 to 16, the driving unit 400 may be installed between the driving module 300 and the reservoir unit 200 and may move the plunger 230 disposed inside the reservoir 210 by using the driving force generated by the driving module 300. However, the driving unit 400 may move the plunger 230 forward only when the rod 410 and the drive wheel 420 are coupled or engaged to each other by the clutch unit 500.

The rod 410 is connected to the plunger 230 and extends in one direction. The rod 410 is inserted into an opening of the cap cover 220, and the rod 410 may move in the lengthwise direction of the reservoir 210 to move the plunger 230. The rod 410 may have a threaded surface. The rod 410 is inserted into the connecting member 520 and, in the case of discharging a fixed amount of a medical liquid, the rod 410 may be engaged with the drive wheel 420 by the clutch unit 500, and thus the rod 410 may be moved forward.

The drive wheel 420 is drivingly connected to the driving module 300 and may rotate by driving the driving module 300. The drive wheel 420 may have a first connection end 421 and a second connection end 422 and may have an inner space in which the rod 410 may move. Since at least one of the first connection end 421 and the second connection end 422 is always drivingly connected to the driving module 300 by a connector CN, the drive wheel 420 may rotate by driving of the driving module 300.

According to an embodiment, the first connection end 421 and the second connection end 422 may each have a gear teeth-like shape. As the connector CN connected to the driving module 300 applies force to gear teeth, the drive wheel 420 may rotate.

In detail, the connector CN rotates repeatedly around a rotation axis according to the linear reciprocating motion of the driving module 300. An end of the connector CN may rotate the drive wheel 420 by applying pressure to at least one of the first connection end 421 and the second connection end 422. For example, a first end of the connector CN may be disposed to apply pressure to the first connection end 421 and a second end of the connector CN may be disposed to apply pressure to the second connection end 422.

When the connector CN rotates around the rotation axis, a second sensor unit 920 may measure the driving of the connector CN. The second sensor unit 920 may measure whether the driving force of the driving module 300 is transmitted to the drive wheel 420 by detecting contact with the connector CN. Also, the second sensor unit 920 may measure the rotated angle of the drive wheel 420 by detecting contact with the connector CN.

The clutch unit 500 may drivingly interconnect the driving module 300 and the driving unit 400. The clutch unit 500 is disposed between the rod 410 and the drive wheel 420 and may include a coupler 510 and the connecting member 520.

Figure 14:
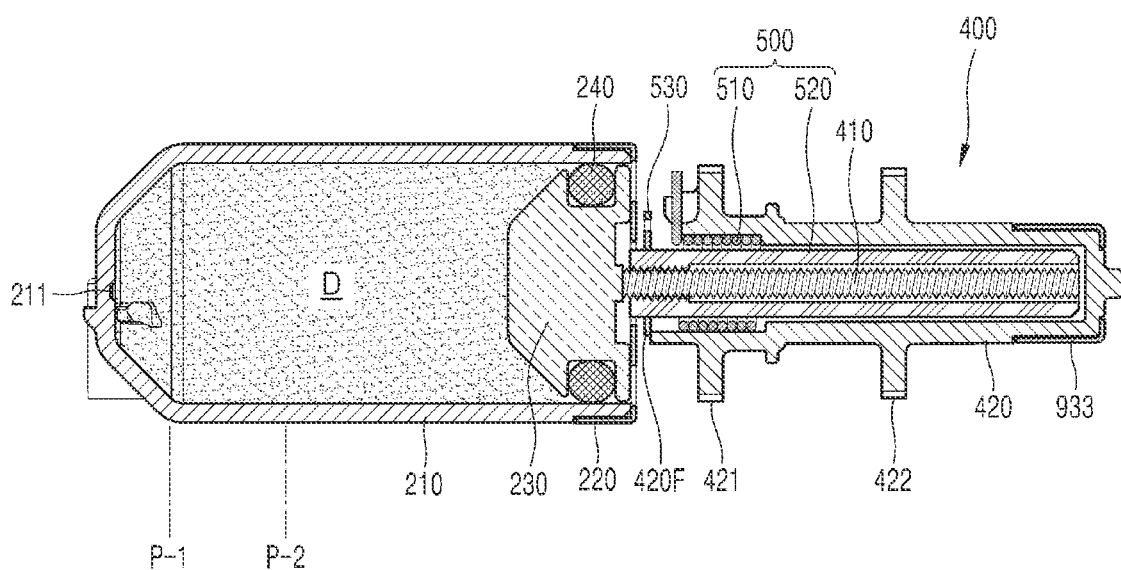
Figure 15:
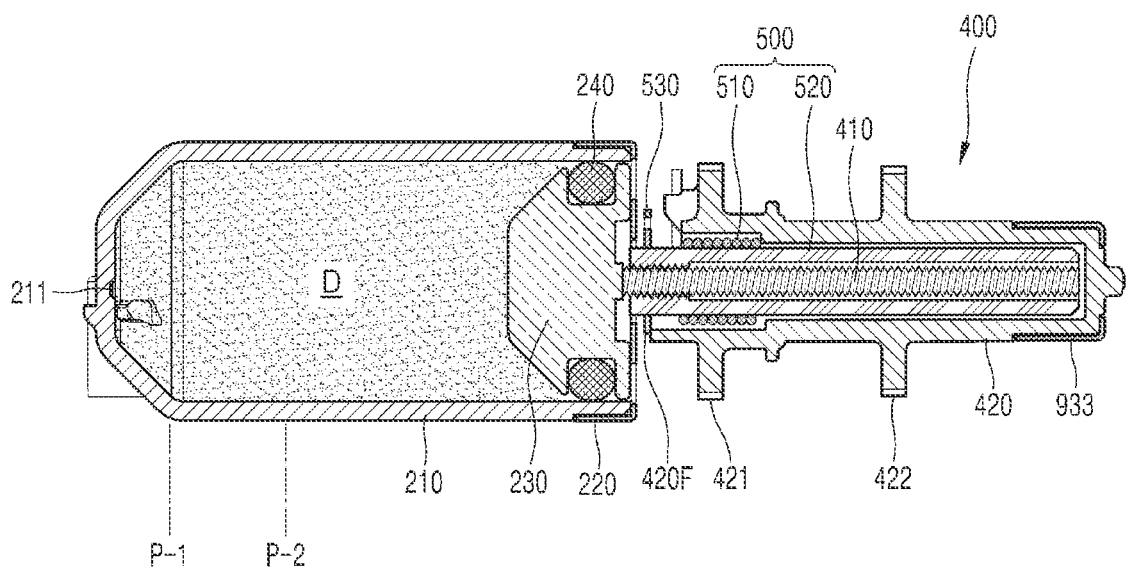
Figure 16:
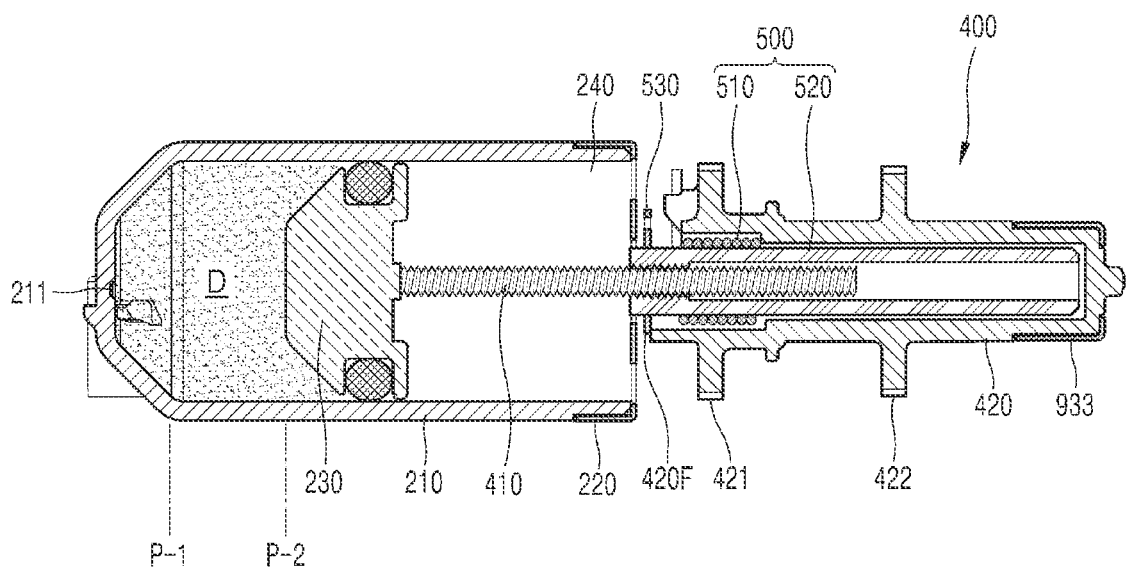

The coupler 510 is disposed outside the connecting member 520, is spaced apart from the connecting member 520 at a certain interval when inactivated (FIGS. 13 and 14), and, when activated, may interconnect the rod 410 and the drive wheel 420 (FIGS. 15 and 16). The coupler 510 is a component capable of applying an elastic force to the outside of the connecting member 520, and the shape thereof is not limited to a specific shape. However, for convenience of explanation, descriptions will be given below based on a case where the coupler 510 has a spring-like shape.

At least a portion of the connecting member 520 may be inserted into the rod 410. The connecting member 520 is disposed to cover the outside of the rod 410. The connecting member 520 may interconnect the driving module 300 and the rod 410 according to the operation of the coupler 510.

According to an embodiment, the rod 410 and the connecting member 520 may have a screw-like shape and a screw thread-like shape, respectively. A screw thread may be formed on the outer circumferential surface of the rod 410 and a screw thread may be formed on the inner circumferential surface of the connecting member 520, and thus the rod 410 and the connecting member 520 may be engaged with each other in a screw-coupling manner.

According to an embodiment, a screw thread may be formed at one end of the connecting member 520, but no screw thread may be formed at the other end of the connecting member 520.

Figure 13:
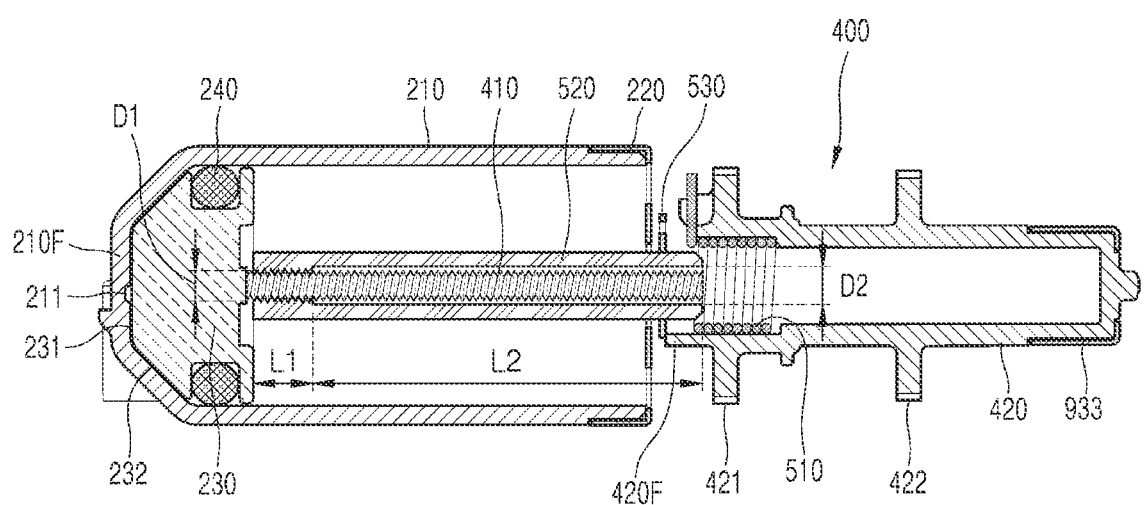
FIGS. 13 to 16 are cross-sectional views of the operation of injecting a medical liquid into a reservoir, storing the medical liquid, and discharging the medical liquid through a needle.

Referring to FIG. 13, a screw thread is formed on the inner circumferential surface of a first section L1 of the connecting member 520, and the rod 410 is screw-coupled only in the first section L1. Also, the diameter of the first section L1 may be D1 in correspondence to that of the rod 410.

No screw thread is formed on the inner circumferential surface of a second section L2 of the connecting member 520. Also, a diameter D2 of the second section L2 may be set to be greater than the diameter D1 of the first section L1. In the second section L2, the connecting member 520 does not contact the rod 410.

The length of the first section L1 may be set, such that the first section L1 overlaps the coupler 510 when the connecting member 520 moves backward. Referring to FIGS. 14 and 15, when the plunger 230 extends to the rearmost position, at least a portion of the first section L1 is disposed to overlap the coupler 510 (i.e., at least a portion of the first section L1 faces the coupler 510). The length of the first section L1 of the connecting member 520 may be set, such that the coupler 510 grips at least a portion of the first section L1 when the coupler 510 is activated.

Since the rod 410 is screw-coupled only in the first section L1 of the connecting member 520, when the connecting member 520 rotates to move the rod 410 forward, the load due to the screw-coupling between the connecting member 520 and the rod 410 may be reduced.

As shown in FIGS. 15 and 16, when the coupler 510 is activated, the coupler 510 grips the connecting member 520, and the connecting member 520 also rotates as the drive wheel 420 rotates. Since the connecting member 520 and the rod 410 are screw-coupled only in the first section L1, even when the drive wheel 420 rotates with a small torque, the connecting member 520 may move the rod 410 forward. In other words, since the rod 410 and the connecting member 520 are screw-coupled only in the first section L1, the plunger 230 may be moved forward even with a slightly weak force by the driving of the driving unit 400. Therefore, the medical liquid injection device 10 may discharge a medical liquid to the needle N even when a small force is generated by the driving module 300, and, since a relatively small driving force is applied to the driving unit 400 and the clutch unit 500, durability of components may be improved.

Figure 17:
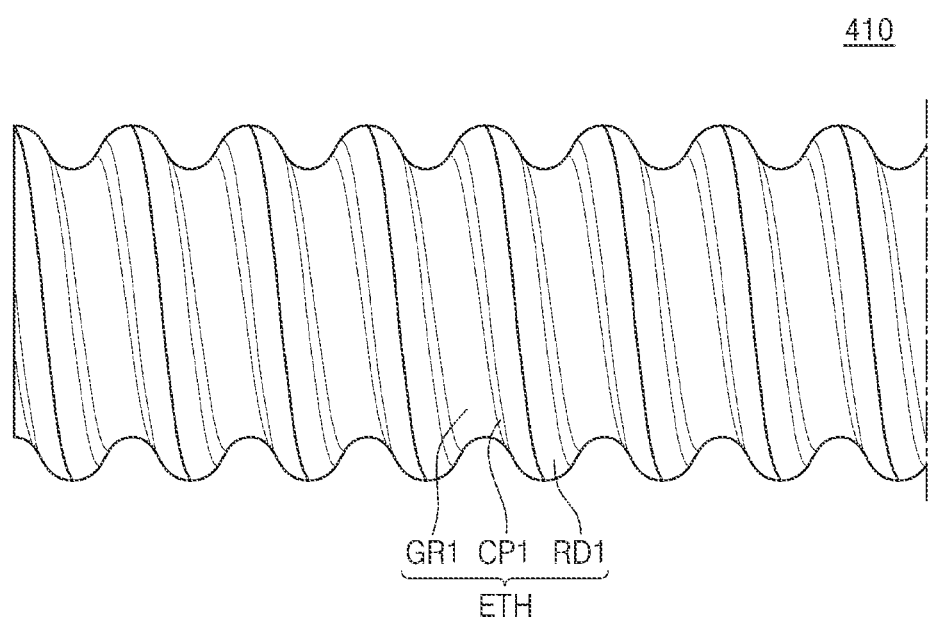
FIG. 17 is a diagram showing a rod of FIG. 13.
Figure 18:
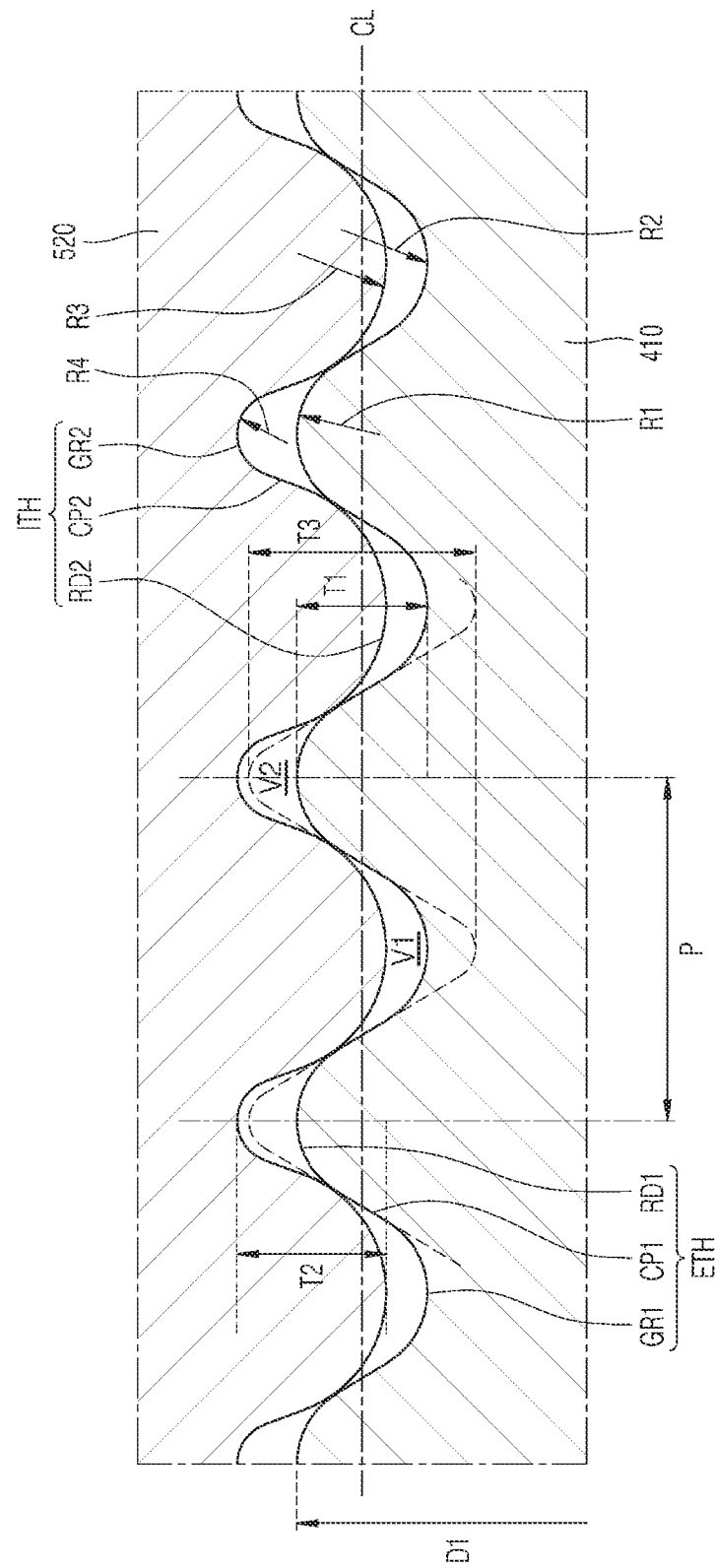
FIG. 18 is a cross-sectional view of a rod and a connecting member to be screw-coupled to each other in FIG. 13.
Figure 19:
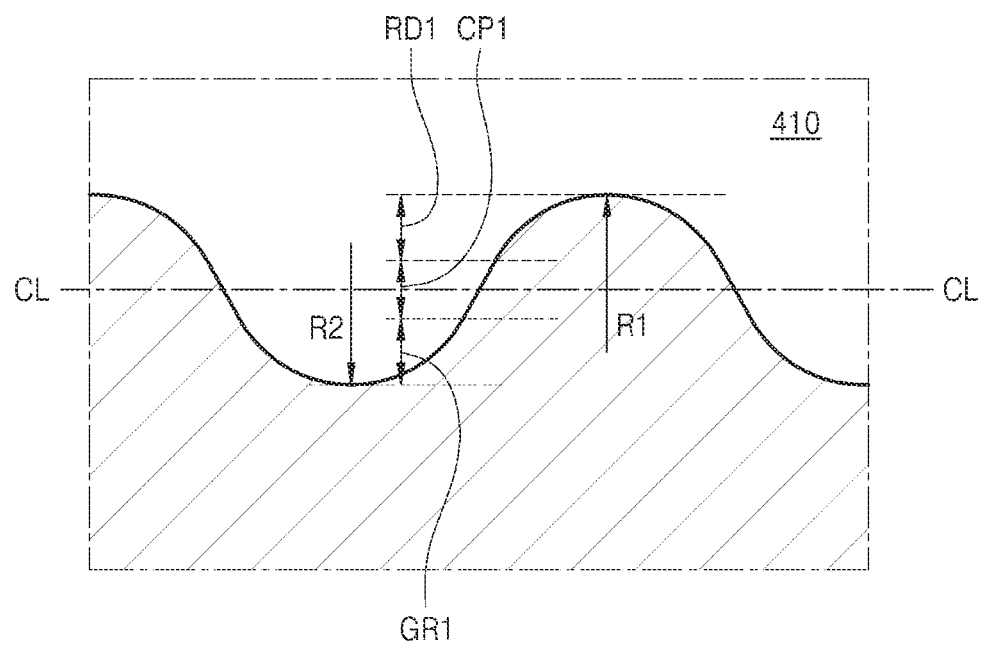
FIG. 19 is a cross-sectional view of a rod of FIG. 17.

FIG. 17 is a diagram showing the rod 410 of FIG. 13, FIG. 18 is a cross-sectional view of the rod 410 and the connecting member 520 of FIG. 13 to be screw-coupled to each other, and FIG. 19 is a cross-sectional view of the rod 410 of FIG. 17.

Referring to FIGS. 17 to 19, the rod 410 and the connecting member 520 are connected to each other screw-coupling, wherein a screw thread and/or a screw groove may be curved to minimize the contact area between a female screw and a male screw.

A male screw ETH may be disposed on the outer circumferential surface of the rod 410. The male screw ETH of the rod 410 may have a first screw thread RD1 and a first screw groove GR1. The first screw thread RD1 may have a first curvature radius R1 having a convex shape, and the first screw groove GR1 may have a second curvature radius R2 having a concave shape.

Also, the male screw ETH of the rod 410 may have a first connection portion CP1 interconnecting the first screw thread RD1 and the first screw groove GR1. The first screw thread RD1 and the first screw groove GR1 each have a certain curvature, but the first connection portion CP1 is defined to have a certain inclination with respect to the lengthwise direction of the rod 410.

A female screw ITH may be disposed on the inner circumferential surface of the connecting member 520. The female screw ITH of the connecting member 520 may have a second screw thread RD2 and a second screw groove GR2. The female screw ITH may be disposed on at least a portion of the inner circumferential surface of the connecting member 520. In FIG. 5, the female screw ITH may be disposed in the section L1 of the connecting member 520. The second screw thread RD2 may have a third curvature radius R3 having a convex shape, and the second screw groove GR2 may have a fourth curvature radius R4 having a concave shape.

Also, the female screw ITH of the connecting member 520 may have a second connection portion CP2 interconnecting the second screw thread RD2 and the second screw groove GR2. The second screw thread RD2 and the second screw groove GR2 each have a certain curvature, but the second connection portion CP2 is defined to have a certain inclination with respect to the lengthwise direction of the connecting member 520.

In the male screw ETH, a distance between first screw threads RD1 adjacent to each other or a distance between first screw grooves GR1 adjacent to each other may be defined as a pitch P. In the female screw ITH, a distance between second screw threads RD2 adjacent to each other or a distance between second screw grooves GR2 adjacent to each other may be defined as a pitch P.

The rod 410 may have a distance between the uppermost point of the first screw thread RD1 and the lowermost point of the first screw groove GR1 as a first height T1 and a distance between the uppermost point of the second screw thread RD2 and the lowermost point of the second screw groove GR2 as a second height T2.

The male screw ETH of the rod 410 is screw-coupled to the female screw ITH of the connecting member 520, wherein the contact area therebetween may be minimized due to curved shapes of the male screw ETH and the female screw ITH. When the rod 410 and the connecting member 520 are screw-coupled to each other, the contact area between the female screw ITH of the connecting member 520 and the surface of the first screw groove GR1 of the rod 410 is minimized, and thus the rod 410 may linearly move even when a small driving force is applied to rotate the connecting member 520.

For example, the rod 410 may contact the female screw ITH of the connecting member 520 only in outer regions in the radial direction at the center of the first height T1 between the first screw thread RD1 and the first screw groove GR1.

For example, the connecting member 520 may contact the male screw ETH of the rod 410 only in inner regions in the radial direction at the center of the second height T2 between the second screw thread RD2 and the second screw groove GR2, that is, only inner regions in directions toward the center of the connecting member 520.

For example, when the male screw ETH and the female screw ITH are coupled, the male screw ETH may form a larger contact area with the female screw ITH on the surface of the first screw thread RD1 than on the surface of the first screw groove GR1. In this case, the female screw ITH may form a larger contact area with the male screw ETH on the surface of the second screw thread RD2 than on the surface of the second screw groove GR2.

For example, when the male screw ETH and the female screw ITH are coupled, the surface of the first screw thread RD1 of the male screw ETH and the surface of the second screw thread RD2 of the female screw ITH may contact each other.

For example, at least one of the surface of the first screw thread RD1 of the male screw ETH and the surface of the first connection portion CP1 and at least one of the surface of the second screw thread RD2 of the female screw ITH and the surface of the second connection portion CP2 may contact each other.

The first height T1 of the rod 410 may be equal to or less than 50% of the pitch P. Compared to a reference RE, which is a conventional screw, of FIG. 9, the uppermost point becomes lower as the end of the first screw thread RD1 is cut according to the first curvature radius R1 and the the lowermost point of the first screw groove GR1 becomes higher as the end of the first screw groove GR1 is filled according to the second curvature radius R2. Therefore, the first height T1 of the rod 410 is smaller than a third height T3 of the reference RE.

The first height T1 of the rod 410 may be set to be smaller than the second height T2 of the connecting member 520. The second height T2 of the connecting member 520 may be set to be smaller than the pitch P and greater than the first height T1 of the rod 410.

For the conventional reference RE, the third height T3 is set to be from about 60% to about 80% of the pitch P and is typically set to be around 70%. For conventional screws, a large contact area is set between a female screw and a male screw to increase the coupling force between two components to be assembled by the screws. To increase the contact area between a female screw and a male screw, a third height is set to be as large as possible.

In the present disclosure, for the rod 410 to linearly move even with a small driving force when the connecting member 520 rotates, the contact area between the female screw ITH and the male screw ETH is reduced, and thus the coupling force between the female screw ITH and the male screw ETH may be reduced. To this end, by reducing the first height T1, a small contact area may be formed between the male screw ETH of the rod 410 and the female screw ITH of the connecting member 520.

According to an embodiment, the first curvature radius R1 of the first screw thread RD1 may be set to be identical to or substantially identical to the second curvature radius R2 of the first screw groove GR1 within a tolerance range.

According to another embodiment, the first curvature radius R1 of the first screw thread RD1 may be set to be different from the second curvature radius R2 of the first screw groove GR1. This will be described in detail below.

The center of the first curvature radius R1 may be set to be lower than the center of the second curvature radius R2. The center of the first curvature radius R1 may be disposed below a center line CL, and the center of the second curvature radius R2 may be disposed above the center line CL.

According to an embodiment, although not shown in the drawings, the third curvature radius R3 of the second screw thread RD2 may be identical to or substantially identical to the fourth curvature radius R4 of the second screw groove GR2 within a tolerance range.

According to another embodiment, the third curvature radius R3 of the second screw thread RD2 may be set to be different from the fourth curvature radius R4 of the second screw groove GR2. For example, as shown in FIG. 9, the third curvature radius R3 may be set to be greater than the fourth curvature radius R4. The first screw thread RD1 may contact the surface of the third curvature radius R3 (the surface of the second screw thread RD2).

When the rod 410 and the connecting member 520 are screw-coupled to each other, a first space V1 may be formed between the first screw groove GR1 and the second screw thread RD2, and a second space V2 may be formed between the first screw thread RD1 and the second screw groove GR2. The sizes of the first space V1 and the second space V2 may be set according to first to fourth curvature radii R1 to R4. Since the first space V1 and the second space V2 form an empty space, a contact area between the female screw ITH and the male screw ETH may be minimized.

At least one of the first curvature radius R1 and the second curvature radius R2 may be set to be different from at least one of the third curvature radius R3 and the fourth curvature radius R4. At least one of the first curvature radius R1 and the second curvature radius R2 may be set to be different from the third curvature radius R3 and the fourth curvature radius R4. Also, at least one of the first curvature radius R1 and the second curvature radius R2 may be set to be between the third curvature radius R3 and the fourth curvature radius R4.

The medical liquid injection device 10 according to an embodiment of the present disclosure may accurately discharge a fixed amount of the medical liquid D. In the medical liquid injection device 10, the driving force generated by the driving module 300 is accurately transferred to the plunger 230, and thus a fixed amount of the medical liquid D may be discharged through the needle N.

In the medical liquid injection device 10 according to an embodiment of the present disclosure, the plunger 230 may linearly move even by a small driving force. Although the rod 410 connected to the plunger 230 is screw-coupled to the connecting member 520, as the contact area between the male screw ETH of the rod 410 and the female screw ITH of the connecting member 520 is reduced, the rod 410 may linearly move even when the connecting member 520 is rotated by a small driving force.

Since a convex curvature is formed at a screw thread or a concave curvature is formed at a screw groove in the male screw ETH of the rod 410 and the female screw ITH of the connecting member 520, the contact area between the female screw ITH and the male screw ETH is reduced, and thus frictional force may be reduced. Therefore, even when a small driving force is transmitted to the connecting member 520, the rod 410 may linearly move.

FIGS. 20 to 24 are cross-sectional views of rods according to other embodiments.

Figure 20:
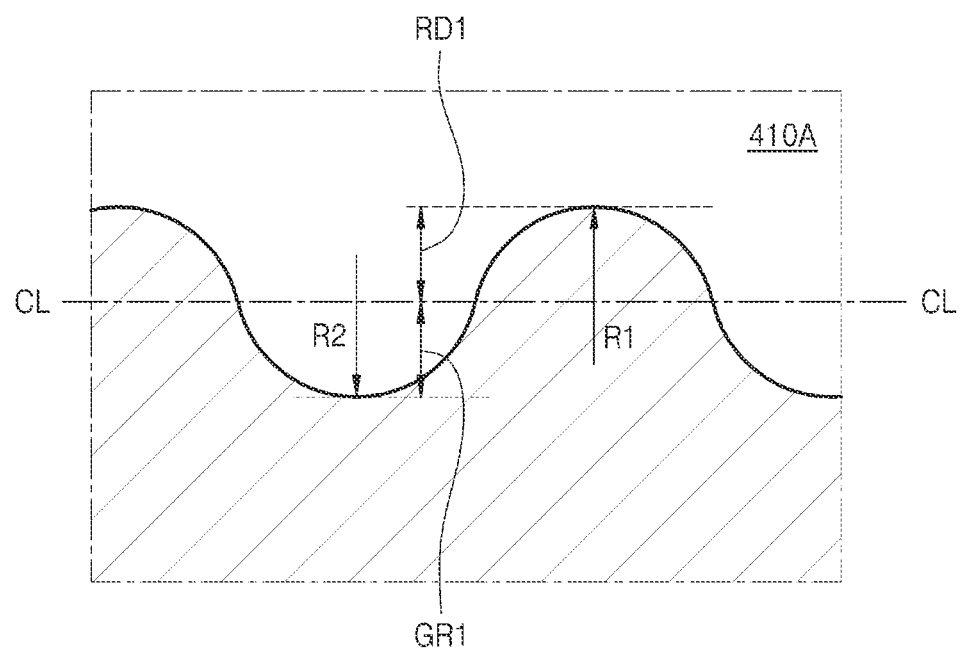
FIGS. 20 to 24 are cross-sectional views of rods according to other embodiments.

Referring to FIG. 20, a rod 410A may have the first screw thread RD1 having the first curvature radius R1 and the first screw groove GR1 having the second curvature radius R2. The first curvature radius R1 and the second curvature radius R2 may be set to be identical to each other or may be substantially identical to each other within a tolerance range.

Compared to the rod 410 of FIG. 19, the rod 410A may be formed, such that the first screw thread RD1 and the first screw groove GR1 each having a certain curvature are connected to each other. A portion of the rod 410A contacting the female screw ITH of the connecting member 520 may be formed only on the surface of the first screw thread RD1 or may be formed larger on the surface of the first screw thread RD1 than on the surface of the first screw groove GR1.

As a first height between the first screw thread RD1 and the first screw groove GR1 is set to be small, the rod 410A may reduce the contact area between the rod 410A and the connecting member 520, and thus, even when the connecting member 520 is rotated by a small driving force, the rod 410A may linearly move.

Figure 21:
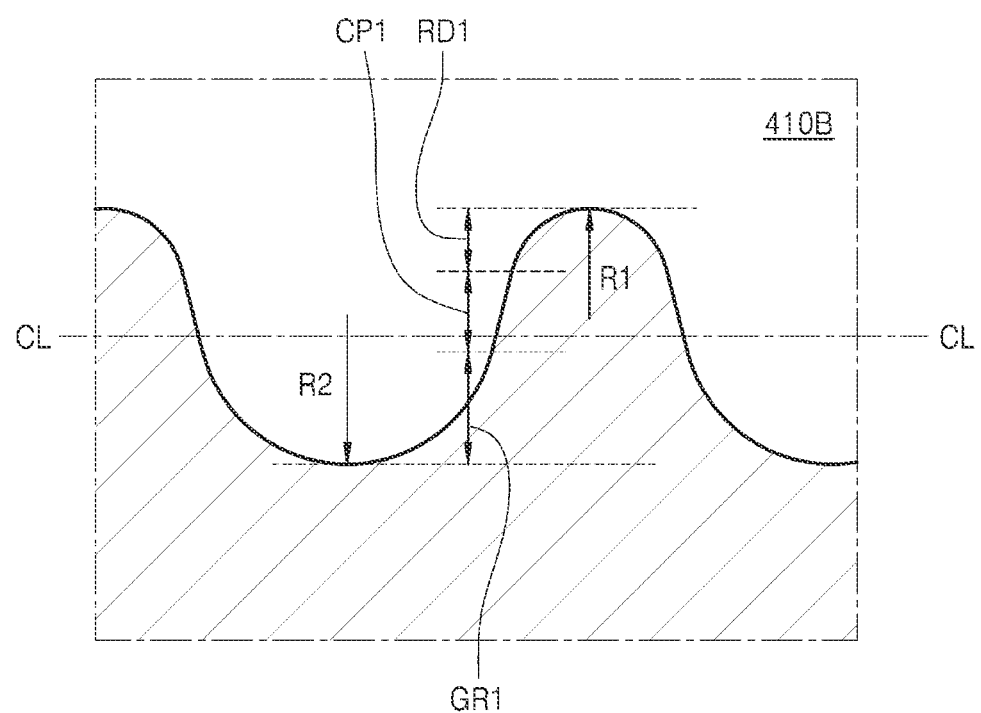

Referring to FIG. 21, a rod 410B may have the first screw thread RD1 having the first curvature radius R1, the first screw groove GR1 having the second curvature radius R2, and the first connection portion CP1 interconnecting the first screw thread RD1 and the first screw groove GR1. The first curvature radius R1 may be set to be smaller than the second curvature radius R2.

For example, when the rod 410B is coupled to the female screw ITH of the connecting member 520, the rod 410B may contact at least one of the surface of the first screw thread RD1 and the surface of the first connection portion CP1. In another example, when the rod 410B is coupled to the female screw ITH of the connecting member 520, the rod 410B may have a larger contact area on the surface of the first screw thread RD1 and/or the surface of the first connection portion CP1 than on the first screw groove GR1.

Figure 22:
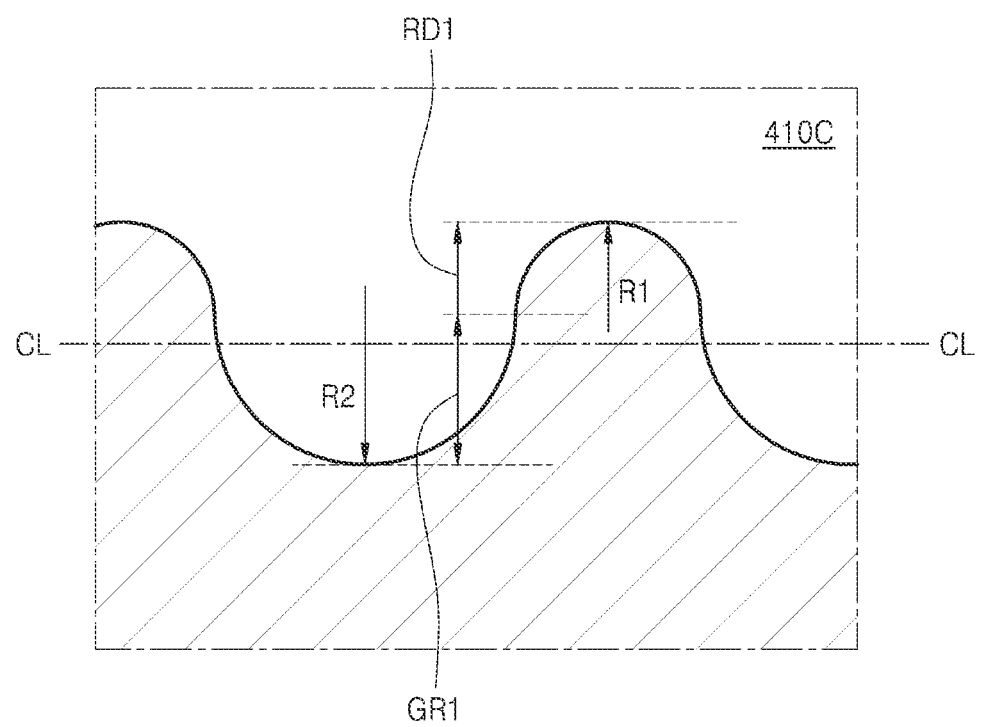

Referring to FIG. 22, a rod 410C may have the first screw thread RD1 having the first curvature radius R1 and the first screw groove GR1 having the second curvature radius R2. The first curvature radius R1 may be set to be smaller than the second curvature radius R2.

Compared to the rod 410B of FIG. 21, the rod 410C may be formed, such that the first screw thread RD1 and the first screw groove GR1 each having a certain curvature are connected to each other. A portion of the rod 410A contacting the female screw ITH of the connecting member 520 may be formed only on the surface of the first screw thread RD1 or may be formed larger on the surface of the first screw thread RD1 than on the surface of the first screw groove GR1.

Figure 23:
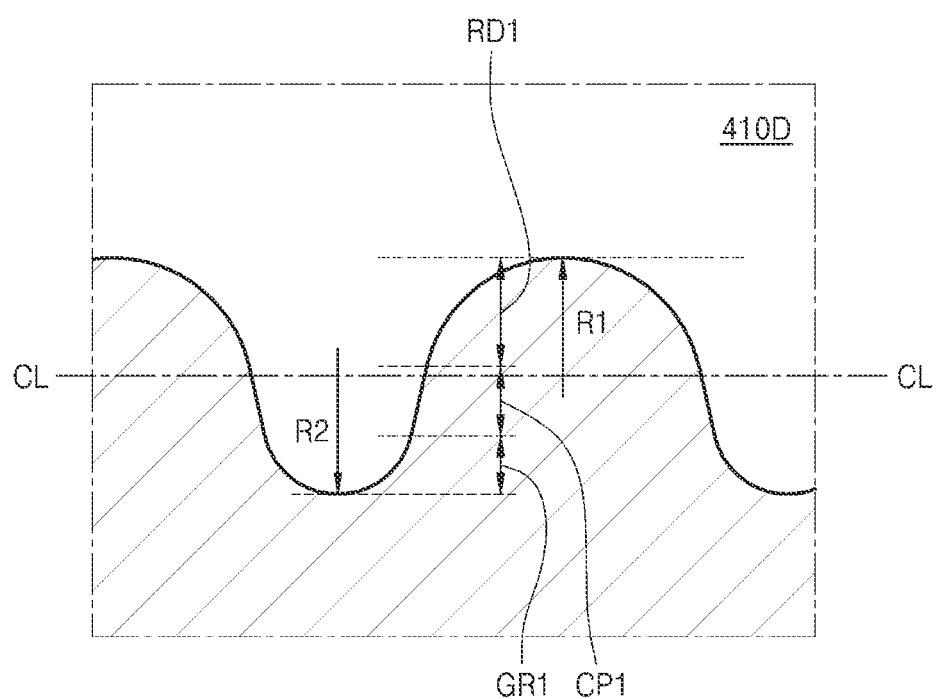

Referring to FIG. 23, a rod 410D may have the first screw thread RD1 having the first curvature radius R1, the first screw groove GR1 having the second curvature radius R2, and the first connection portion CP1 interconnecting the first screw thread RD1 and the first screw groove GR1. The first curvature radius R1 may be set to be greater than the second curvature radius R2.

For example, when the rod 410D is coupled to the female screw ITH of the connecting member 520, the rod 410D may contact at least one of the surface of the first screw thread RD1 and the surface of the first connection portion CP1. The female screw ITH of the connecting member 520 may be coupled only to the surface of the first screw thread RD1 of the rod 410D. In another example, when the rod 410D is coupled to the female screw ITH of the connecting member 520, the rod 410D may have a larger contact area on the surface of the first screw thread RD1 and/or the surface of the first connection portion CP1 than on the first screw groove GR1.

Figure 24:
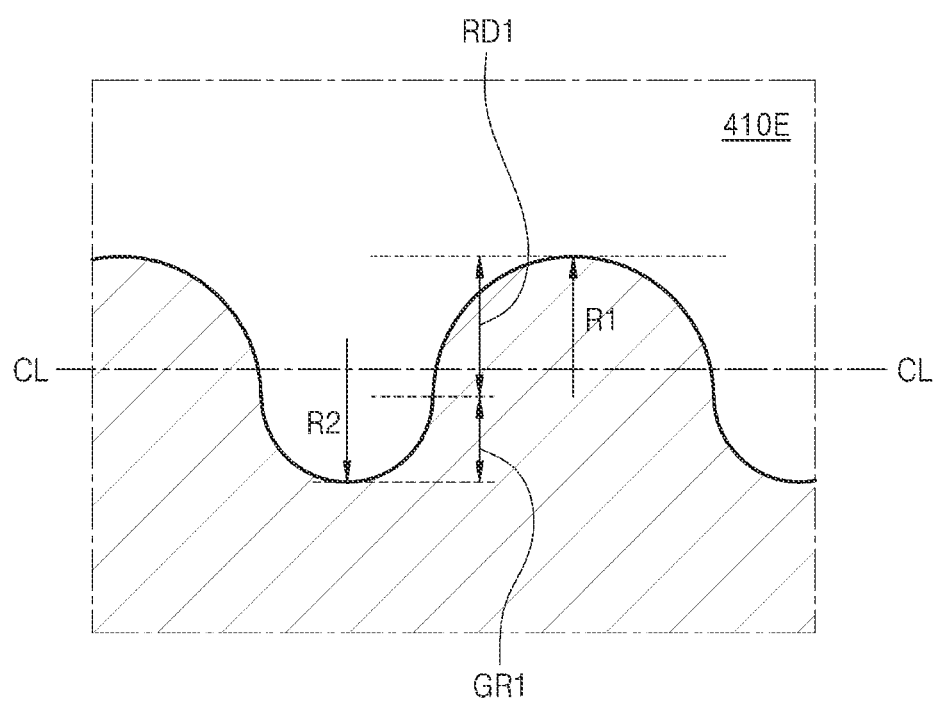

Referring to FIG. 24, a rod 410E may have the first screw thread RD1 having the first curvature radius R1 and the first screw groove GR1 having the second curvature radius R2. The first curvature radius R1 may be set to be greater than the second curvature radius R2.

Compared to the rod 410D of FIG. 23, the rod 410E may be formed, such that the first screw thread RD1 and the first screw groove GR1 each having a certain curvature are connected to each other. A portion of the rod 410A contacting the female screw ITH of the connecting member 520 may be formed only on the surface of the first screw thread RD1 or may be formed larger on the surface of the first screw thread RD1 than on the surface of the first screw groove GR1.

Figure 25:
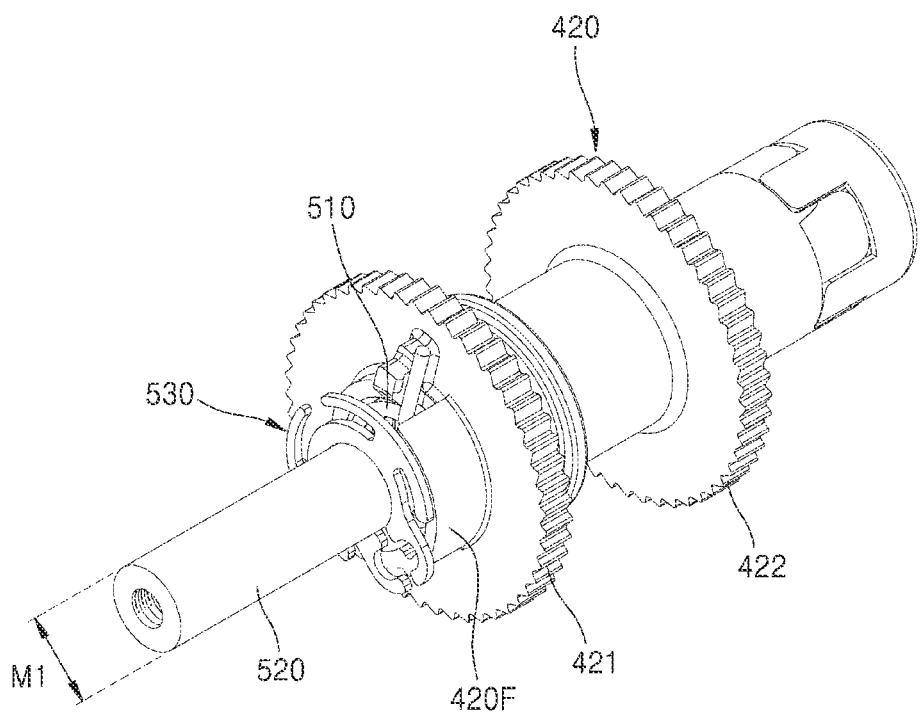
FIG. 25 is a perspective view of some of the components of FIG. 3 to which a resistance member is assembled.
Figure 26:
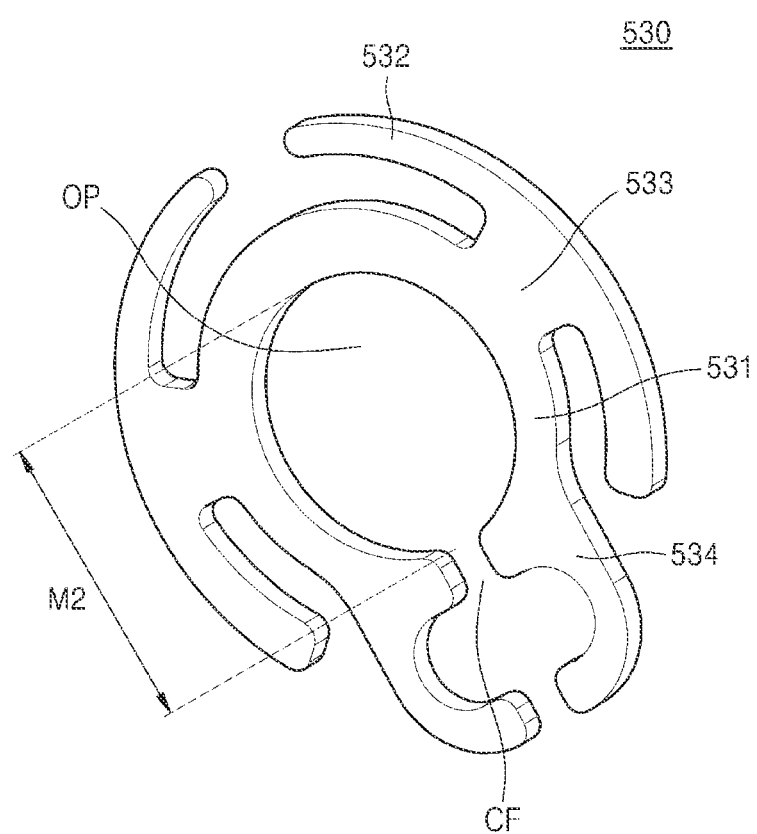
FIG. 26 is a perspective view of the resistance member of FIG. 25.

FIG. 25 is a perspective view of some of components of FIG. 3 to which a resistance member 530 is assembled, and FIG. 26 is a perspective view of the resistance member 530 of FIG. 25.

Referring to FIGS. 25 and 26, the resistance member 530 may be inserted into the connecting member 520. The resistance member 530 may contact the connecting member 520 and generate frictional force when the connecting member 520 retreats.

The resistance member 530 is inserted into the connecting member 520 and may be configured in various ways as a component that generates resistance to the connecting member 520. Although the drawings show that the resistance member 530 has an opening in the center and has a thin plate-like shape, the present disclosure is not limited thereto, and the resistance member 530 may be configured in various ways. For example, the resistance member 530 may be formed as silicon inserted outside the connecting member 520. Also, the resistance member 530 may be a spring interconnecting the cap cover 220 and the connecting member 520, and the spring may resist the connecting member 520 from retracting. However, for convenience of explanation, an embodiment in which the resistance member 530 has a plate-like shape will be mainly described below.

The resistance member 530 may include an insertion opening OP through which the connecting member 520 is inserted and a base portion 531 extending outward of the insertion opening OP. Also, the resistance member 530 may have a cutout CF, which is formed at one side of the base portion 531 and connected to the insertion opening OP.

The connecting member 520 may be installed to pass through the insertion opening OP of the resistance member 530. The resistance member 530 may be disposed between the rear end of the reservoir 210 and the drive wheel 420. The plunger 230 in the reservoir 210 is connected to the rod 410, and the rod 410 is inserted into the connecting member 520. The drive wheel 420 is spaced apart from the rear end of the reservoir 210, and the connecting member 520 may be inserted into the inner space of the reservoir 210.

When the plunger 230 and the connecting member 520 move to the rear of the reservoir 210, one side of the resistance member 530 may be supported by the drive wheel 420. The resistance member 530 is disposed between the reservoir 210 and the drive wheel 420 and may move together with the connecting member 520 until the resistance member 530 contacts a front end 420F of the drive wheel 420 when the connecting member 520 moves. When the base portion 531 of the resistance member 530 contacts the front end 420F of the drive wheel 420, even when the connecting member 520 moves rearward, retraction of the resistance member 530 is prevented by the front end 420F and the resistance member 530 may form a resistance (frictional force) in a direction opposite to the moving direction of the connecting member 520. In other words, the resistance member 530 may generate frictional force on the outer circumferential surface of the connecting member 520.

The base portion 531 extends to the outside the insertion opening OP and may have a certain thickness. The base portion 531 may be supported by the drive wheel 420.

Wing ends 532 may be arranged outside the base portion 531. Although FIG. 10 shows two wing ends 532, the present disclosure is not limited thereto, and one, three, or more wing ends 532 may be provided. The wing ends 532 may be supported by the drive wheel 420 and receive resistance from the drive wheel 420.

A connection end 533 may interconnect the base portion 531 and the wing ends 532. The connection end 533 may have a certain thickness, thereby evenly distributing resistance force transmitted from the base portion 531 and the wing ends 532.

Cut ends 534 extends outward from the base portion 531, and the cutout CF may be disposed. The cut ends 534 may be spaced apart from one another to form the cutout CF.

The connecting member 520 is inserted into the insertion opening OP, and, as shown in FIG. 10, according to an embodiment, the insertion opening OP may be formed in a circular shape. According to another embodiment, the insertion opening OP may be formed in a polygonal shape. According to another embodiment, in the insertion opening OP, a plurality of protrusions protruding from the inner circumferential surface of the base portion 531 toward the center (of the base portion 531?) may be arranged. The plurality of protrusions may contact the outer circumferential surface of the connecting member 520.

A minimum diameter M2 of the insertion opening OP may be set to be smaller than a diameter M1 of the connecting member 520. To tightly assemble the insertion opening OP to the connecting member 520, the minimum diameter M2 of the insertion opening OP may be set to be smaller than the diameter M1 of the connecting member 520. Therefore, when the resistance member 530 contacts the drive wheel 420, a resistance force may be generated on the connecting member 520.

The cutout CF is formed by cutting one side of the base portion 531 and may be connected to the insertion opening OP. The cutout CF may form an elastic force on the resistance member 530.

Referring to FIGS. 13 and 14, when the medical liquid D is injected into the reservoir 210, the plunger 230, the rod 410, and the connecting member 520 are retracted toward the drive wheel 420. When the plunger 230 and the connecting member 520 are retracted due to the injection of the medical liquid D into the reservoir 210, the resistance member 530 contacts the drive wheel 420 and generates a resistance force on the connecting member 520.

Only when the medical liquid D is injected into the reservoir 210 with a greater pressure that overcomes the resistance force, the medical liquid D may be injected into the reservoir 210 as the connecting member 520 is retracted. Since the medical liquid D is injected and stored in the reservoir 210 at a high pressure that overcomes a resistance force, the medical liquid D stored in FIG. 6 has a high pressure.

As shown in FIG. 15, when the coupler 510 of the clutch unit 500 grips the connecting member 520 and the drive wheel 420 rotates, the medical liquid D may be quickly discharged through the needle N. Since the medical liquid D stored in the reservoir 210 is stored at a higher pressure than the external pressure, even when a small driving force is transmitted from the driving module 300, the plunger 230, the rod 410, and the connecting member 520 may move forward, and thus a fixed amount of the medical liquid D may be discharged through the needle N.

Figure 27:
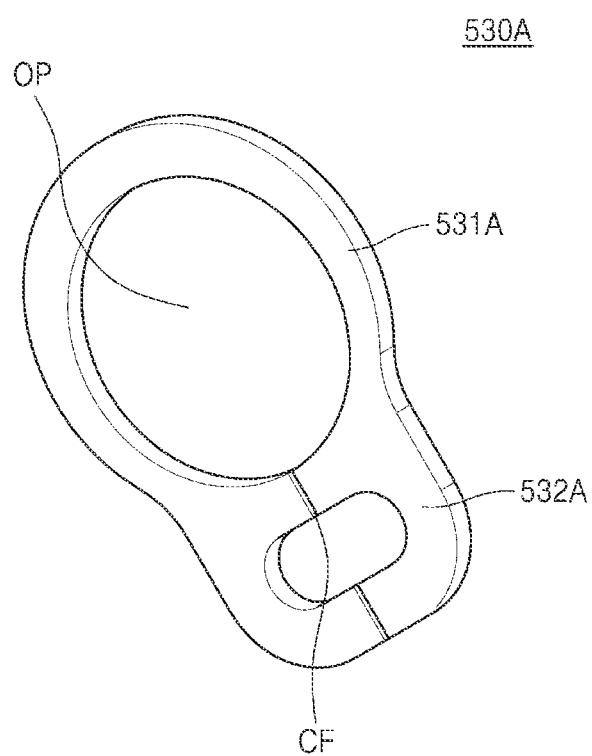
FIG. 27 is a perspective view of a modified example of the resistance member of FIG. 26.

FIG. 27 is a perspective view of a modified example of the resistance member of FIG. 26.

Referring to FIG. 27, a resistance member 530A may have the insertion opening OP, the cutout CF, a base portion 531A, and a cut end 532A. The connecting member 520 is inserted into the insertion opening OP, and the base portion 531A extends along the insertion opening OP and, when the connecting member 520 moves, may contact the front end 420F of the drive wheel 420. The cutout CF is formed by cutting the base portion 531 and may be disposed between cut ends 532A facing each other.

The resistance member 530A is inserted into the connecting member 520 and generates a resisting force on the connecting member 520 when the medical liquid D is injected into the reservoir 210, and thus the medical liquid D is stored in the reservoir 210 at a high pressure.

According to another embodiment, the resistance member 530A is installed together with the above-stated resistance member 530 to generate a greater resistance force on the connecting member 520, and thus the medical liquid D may be stored in the reservoir 210 at a higher pressure.

Referring back to FIG. 3, the trigger member 600 may generate a mechanical signal for injecting a medical liquid of the medical liquid injection device 10. The trigger member 600 may be rotatably disposed on one side of the third body 15. The trigger member 600 rotates to start driving the driving module 300, and, at the same time, the clutch unit 500 may drivingly be connected to the driving unit 400.

The trigger member 600 may be rotated in one direction around a rotation axis. At this time, the trigger member 600 may apply force to the clutch unit 500 to couple a rod and the drive wheel 420 to each other.

In detail, when a user rotates the needle assembly 100, the knob of the needle assembly 100 applies a force to the end of the trigger member 600, and thus rotation of the trigger member 600 may be initiated. When the trigger member 600 rotates, the trigger member 600 applies a force to the end of the coupler 510, and the coupler 510 is coupled to the connecting member 520. Therefore, the clutch unit 500 is activated.

The needle cover assembly 700 may be attached below needle assembly 100. The needle cover assembly 700 may prime the air stored in the reservoir unit 200 before injecting a medical liquid. Through the medical liquid injector NI, when the medical liquid is injected into the reservoir 210, a gas (air) remaining in the reservoir 210 may be discharged to the outside.

The needle cover assembly 700 may have a first cover 710, a second cover 720, a filter member 730, and an adhesive layer 740.

The first cover 710 may be disposed under the medical liquid injection device 10. The second cover 720 may be inserted and assembled into an opening of the first cover 710. An insertion protrusion 711 inserted into the second body 14 to fix the needle cover assembly 700 may be disposed on one side of the first cover 710.

The second cover 720 is assembled to the first cover 710, and the needle N and/or a cannula may be aligned to the center of the second cover 720. The second cover 720 penetrates at the center thereof in the heightwise direction and may have a storage space in which the medical liquid D is stored.

The first cover 710 has greater rigidity than the second cover 720. The first cover 710 is a portion exposed to the outside and includes a material with a slightly greater rigidity than that of the second cover 720. The second cover 720 is assembled to the first cover 710 and includes a material having less rigidity than the first cover 710 to be inserted into an opening of the third body 15.

A protrusion 721 to be inserted into the third body 15 may be provided at the center of the second cover 720. Also, the second cover 720 has a fixing protrusion 722, and, as the fixing protrusion 722 is inserted into the first cover 710, the first cover 710 and the second cover 720 may be assembled.

The protrusion 721 of the second cover 720 is inserted into an opening at the bottom of the third body 15. A diameter G2 of the protrusion 721 is set to be slightly greater than a diameter G1 of the opening. Since the second cover 720 has a certain elasticity, the protrusion 721 may be inserted into the opening and fixed.

The second cover 720 has an inner diameter G3, and thus the needle N and the cannula C may be aligned above the second cover 720. The inner diameter G3 forms a storage space of the second cover 720, and a medical liquid may be stored therein or a gas may be moved and discharged therefrom.

The filter member 730 is attached to the second cover 720. The filter member 730 is disposed under the storage space of the second cover 720, and a gas like air passes through the filter member 730, but a liquid like a medical liquid does not pass through the filter member 730. Therefore, the air discharged from the needle N passes through the filter member 730 and is discharged to the outside, but a medical liquid discharged from the needle may be stored in the storage space defined by the second cover 720 and the filter member 730.

The shape of the filter member 730 may change according to the amount of a medical liquid stored in the storage space. For example, when the storage space is filled with a medical liquid, the filter member 730 expands downward, and thus a user may recognize that the medical liquid has flowed into the needle cover assembly 700.

The adhesive layer 740 is disposed on one surface of the needle cover assembly 700 and may attach the needle cover assembly 700 to the attachment portion 12.

Referring to FIGS. 4, 13, and 14, an operation of priming a gas remaining in the reservoir 210 while storing a medical liquid in the reservoir unit 200 will be described below.

As shown in FIG. 13, before injection of a medical liquid, the plunger 230 is disposed at the front end of the reservoir 210, and the rod 410 is assembled to the connecting member 520 at the rear end of the plunger 230. At this time, since the coupler 510 does not grip the connecting member 520, the drive wheel 420 is not connected to the rod 410.

A user puts the medical liquid D to be injected in the medical liquid injector NI and inserts the medical liquid injector NI into the inlet end 210I of the reservoir unit 200. At this time, the air remaining inside the reservoir 210 may be primed.

In detail, during the assembly of the reservoir unit 200, the air remains between the reservoir 210 and the plunger 230. When the medical liquid D is injected while the air remains in the reservoir 210, there is a risk that the air will also be injected into a user, and thus an operation of removing the air (priming operation) is needed.

When the medical liquid D starts flowing into the reservoir 210 from the medical liquid injector NI, the medical liquid D flows between the inner surface of the reservoir 210 and the plunger 230 and pushes out the remaining gas to the needle N. At this time, the gas may move along the guide groove 211. In other words, the gas remaining inside the reservoir 210 may be pushed by the medical liquid D flowing into the reservoir 210, guided by the guide groove 211, and discharged to the needle N. The gas passed through the needle N moves to the needle cover assembly 700, passes through the filter member 730 of the needle cover assembly 700, and is discharged to the outside.

By being guided by the guide groove 211, the gas remaining inside the reservoir 210 is quickly discharged to the outside, and thus the gas in the reservoir 210 may be removed.

Thereafter, as shown in FIG. 14, the medical liquid D flows into the inner space of the reservoir 210, pushes the plunger 230 backward, and is stored in the inner space of the reservoir 210.

When the gas is completely removed, the medical liquid D may be discharged through the needle N. Since the medical liquid D does not pass through the filter member 730, the medical liquid D is stored in the storage space of the needle cover assembly 700. Since the shape of the filter member 730 may be deformed, when the medical liquid D is stored in the storage space, the filter member 730 may protrude downward. The user may check whether the filter member 730 protrudes, thereby determining whether there is no gas inside the reservoir unit 200 and whether the medical liquid is stored in the reservoir 210.

The medical liquid injection device 10 according to an embodiment of the present disclosure may safely inject a medical liquid into a user. The medical liquid injection device 10 may remove a gas from the reservoir 210 and safely store a medical liquid in the reservoir 210, thereby eliminating the risk of injecting gas into the user. The guide groove 211 is disposed on the inner surface of the reservoir 210, and, when a medical liquid is injected into the reservoir 210 to store the medical liquid, the gas inside the reservoir 210 may be quickly and completely discharged to the outside along the guide groove 211.

The alarm unit 800 is disposed inside or outside the medical liquid injection device 10 and may notify a user of normal operation or malfunction of the medical liquid injection device 10.

For example, the alarm unit 800 is disposed below the housing 11 and is connected to a circuit board. The alarm unit 800 may generate a warning sound or emit light to deliver an alarm to a user.

Referring to FIG. 4, a plurality of sensor units may measure the driving of the medical liquid injection device 10. The plurality of sensor units may measure a storage amount of a medical liquid in the reservoir 210, whether the driving module 300 is driven, whether the driving unit 400 is driven, a rotational angle of the drive wheel 420, and a moving distance of the plunger 230.

Each sensor unit may have a plurality of contact ends. Contact ends may measure events or data by measuring electrical contacts thereto, respectively.

The position of one end of a contact end may be changed by contact with another component and may return to its original position by restoring force when contact with the other component is released.

According to an embodiment, a contact end may have an elastic spring-like shape. A contact end may have a first end connected to the control module 16, which is a circuit board, and a second end extending from the first end and contacting the connecting member 520.

A diameter of the first end may be set to be greater than a diameter of the second end. Since the diameter of the first end is greater than the diameter of the second end, the first end may be firmly supported on the circuit board. The first end is stably supported by the control module 16, and the position or the shape of the second end is easily changed to stably maintain contact with another component.

A length of the first end may be set to be smaller than a length of the second end. Since the length of the first end is smaller than the length of the second end, the first end may be firmly supported on the circuit board. The first end is stably supported by the control module 16, and the position or the shape of the second end is easily changed to stably maintain contact with another component.

In particular, since the diameter of the second end is set to be smaller than the diameter of the first end or the length of the second end is set to be greater than the length of the first end, even when the second end contacts another component like the connecting member 520, a base cover 933, etc., the position or the shape of the second end may be easily changed to stably maintain contact with the other component.

The first sensor unit 910A is disposed adjacent to the reservoir unit 200. The first sensor unit 910A may be disposed on a moving path of the connecting member 520. The first sensor unit 910A may have a plurality of contact ends, and the plurality of contact ends may be attached in a fixing groove 14A of the second body 14. While the connecting member 520 is moving, the connecting member 520 may contact at least one of the plurality of contact ends.

According to an embodiment, the first sensor unit 910A may include a first contact end 911 and a second contact end 912. The first contact end 911 and the second contact end 912 are arranged to be spaced apart from each other, and the connecting member 520 may linearly move and contact the first contact end 911 and/or the second contact end 912.

The connecting member 520 may contact the first contact end 911 at a first position P1 and contact the second contact end 912 at a second position P2.

Referring to FIGS. 4, 5, and 6, in the process of injecting the medical liquid D into the reservoir 210, the connecting member 520 first contacts the first contact end 911 at the first position P1 (the plunger 230 is at a position P-1), and then the connecting member 520 contacts the second contact end 912 at the second position P2 (the plunger 230 is at a position P-2).

According to an embodiment, the connecting member 520 may electrically interconnect the first contact end 911 and the second contact end 912. When the first contact end 911 and the second contact end 912 are electrically connected to each other through the connecting member 520, the control module 16 may recognize a specific event of the reservoir unit 200.

For example, when the connecting member 520 contacts the first contact end 911 and the second contact end 912, the first sensor unit 910A may sense that a medical liquid stored in the reservoir 210 at a first reference amount (e.g., 10%, 20%, 30%, etc.).

When it is recognized that the medical liquid D is stored in the reservoir 210 at the set first reference amount, the control module 16 may wake up the medical liquid injection device 10. In other words, the control module 16 may check that a certain amount of medical liquid is stored in the reservoir 210 and start partial driving to pre-heat the medical liquid injection device 10 (first mode).

According to another embodiment, the connecting member 520 may contact at least one of contact ends of the first sensor unit 910A and generate an electrical signal. When the connecting member 520 contacts the first contact end 911, the control module 16 may recognize a first event. When the connecting member 520 contacts the second contact end 912, the control module 16 may recognize a second event.

For example, the connecting member 520 may contact the first contact end 911 to wake up the medical liquid injection device 10 and contact the second contact end 912 to sense a storage amount of a medical liquid stored in the medical liquid injection device 10.

For example, the connecting member 520 may contact the first contact end 911 to wake up the medical liquid injection device 10 and primarily sense the amount of medical liquid stored in the reservoir 210, and then may contact the second contact end 912 to secondarily sense the storage amount of the medical liquid stored in the medical liquid injection device 10.

As shown in FIGS. 4, 7, and 8, in the process of discharging the medical liquid D to the needle N, the connecting member 520 first releases contact with the second contact end 912 at the second position P2 (the plunger 230 is at the position P-2), and then the connecting member 520 releases contact with the first contact end 911 at the first position P1 (the plunger 230 is at the position P-1).

According to an embodiment, when the connecting member 520 maintains contact with the first contact end 911 and the second contact end 912 and the contact with the second contact end 912 is released, the first contact end 911 and the second contact end 912 are disconnected electrically. When the first contact end 911 and the second contact end 912 are electrically disconnected, the control module 16 may recognize a specific event of the reservoir unit 200.

In detail, when the second contact end 912 is disconnected, the control module 16 may generate a signal indicating that the medical liquid D stored in the reservoir 210 is insufficient. The control module 16 may generate an alarm signal and transmit the alarm signal to the controller 30, the user terminal 20, and/or the alarm unit 800, and thus the user may recognize the amount of the medical liquid.

Also, when a third mode is set in the medical liquid injection device 10, the distance that the plunger 230 moved forward inside the reservoir 210 is precisely measured by using the second sensor unit 920 and/or an encoder unit 930, thereby precisely measuring and monitoring the amount of the medical liquid stored in the reservoir 210.

According to another embodiment, the connecting member 520 may release contact with at least one of the contact ends of the first sensor unit 910A, thereby recognizing different events. When the connecting member 520 releases contact with the second contact end 912, the control module 16 may recognize a third event. When the connecting member 520 releases contact with the first contact end 911, the control module 16 may recognize a fourth event.

For example, when the connecting member 520 releases contact with the second contact end 912, the control module 16 may transmit an alarm signal to a user. When the connecting member 520 releases contact with the first contact end 911, the control module 16 may forcibly terminate the medical liquid injection device 10, continuously generate alarm signals to the user terminal 20, reduce the amount of the medical liquid injected into the user, or increase the injection period.

The second sensor unit 920 may sense whether the driving module 300 and/or the driving unit 400 is/are driven. The driving module 300 and the drive wheel 420 are drivingly connected to each other by the connector CN. When the driving module 300 moves linearly, the connector CN rotates repeatedly around the rotation axis, and both ends of the connector CN alternately apply forces to the first connection end 421 and the second connection end 422 of the drive wheel 420, and thus the drive wheel 420 rotates. The second sensor unit 920 may determine whether the connector CN rotates around the rotation axis and measure the number of rotations.

The second sensor unit 920 may measure the moving distance of the plunger 230, the discharged amount of the medical liquid discharged through the needle N, and the amount of the medical liquid remaining in the reservoir 210. The second sensor unit 920 measures a degree that the connector CN rotates the drive wheel 420. When the rotational angle of the drive wheel 420 is measured by the second sensor unit 920, a distance that the plunger 230 linearly moved may be calculated, and the discharged amount of the medical liquid discharged from the reservoir 210 and the amount of the medical liquid remaining in the reservoir 210 may be measured based on the distance.

The second sensor unit 920 may have a 1A contact end 921 and a 2A contact end 922. When the connector CN contacts the 1A contact end 921, the second sensor unit 920 determines that the connector CN has applied a force to any one of the first connection end 421 and the second connection end 422. When the connector CN contacts the 2A contact end 922, the second sensor unit 920 determines that the connector CN has applied a force to the other one of the second connection end 422 and the second connection end 422.

The encoder unit 930 may be disposed at one end of the driving unit 400 and measure rotation of the driving unit 400. The encoder unit 930 may measure rotation of the drive wheel 420.

The encoder unit 930 may have the base cover 933 having a 1B contact end 931, a 2B contact end 932, a cover end 933A, and a teeth end 933B.

The 1B contact end 931 is disposed at the end of the base cover 933 and may always maintain contact with the base cover 933. The 1B contact end 931 may selectively maintain contact with the cover end 933A.

Although the drawing shows that the 1B contact end 931 is disposed on the opposite side of the 2B contact end 932, the present disclosure is not limited thereto. For example, the 1B contact end 931 and the 2B contact end 932 may be arranged on the same side of the drive wheel 420. Also, the 1B contact end 931 may be disposed behind the drive wheel 420.

The 2B contact end 932 is disposed at the end of the base cover 933 to be spaced apart from the 1B contact end 931. The 2B contact end 932 is disposed to contact the teeth end 933B and may contact the teeth end 933B or release contact with the teeth end 933B according to rotation of the drive wheel 420.

The base cover 933 is inserted into one end of the drive wheel 420. The cover end 933A extends to go around the outer circumferential surface of the drive wheel 420, but a plurality of teeth ends 933B may extend from the cover end 933A to be spaced apart from one another along the outer circumferential surface of the drive wheel 420. The teeth end 933B may extend in the lengthwise direction of the drive wheel 420 from the cover end 933A.

The encoder unit 930 may determine whether the second sensor unit 920 is properly driven by sensing the rotation of the drive wheel 420. When the rotation of the drive wheel 420 is detected by the encoder unit 930 when the medical liquid injection device 10 is normally operating, the second sensor unit 920 also needs to contact the connector CN. When the encoder unit 930 detects that the drive wheel 420 does not rotate, there should be no contact between the second sensor unit 920 and the connector CN. Therefore, by comparing a signal detected by the encoder unit 930 and a signal detected by the second sensor unit 920, the encoder unit 930 may check an error of the second sensor unit 920.

Figure 28:
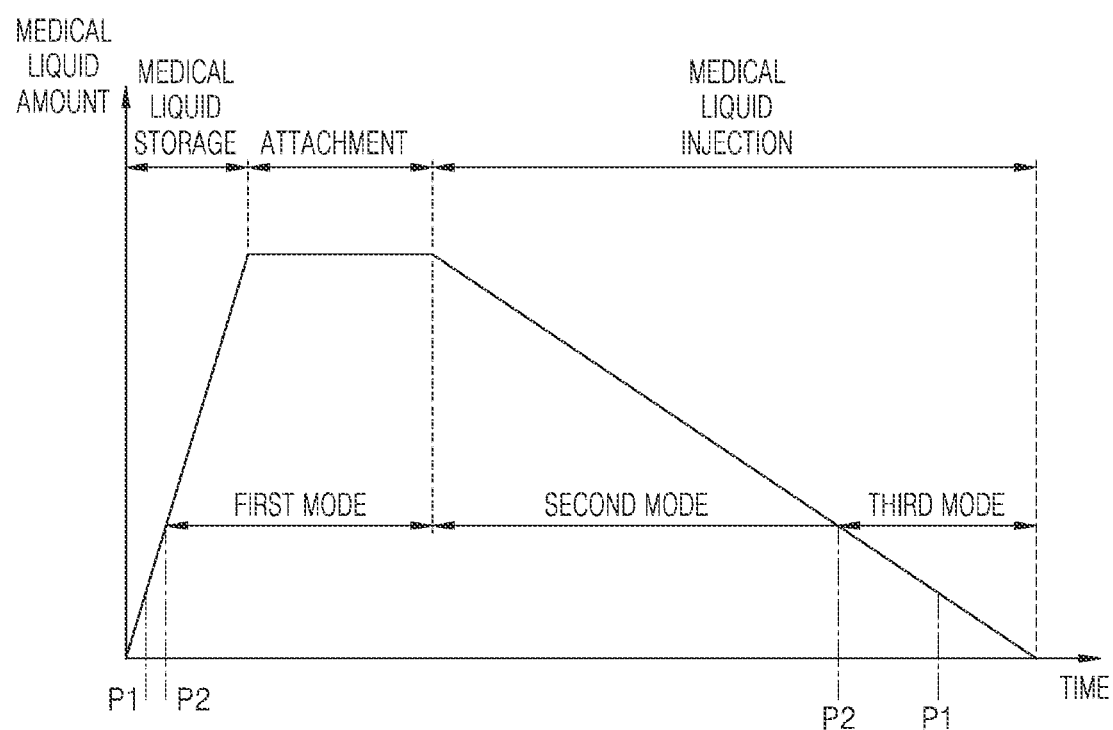
FIG. 28 is a graph showing a change in the amount of medical liquid and a change in a driving mode according to driving of a medical liquid injection device.

FIG. 28 is a graph showing a change in the amount of medical liquid and a change in a driving mode according to driving of a medical liquid injection device.

Referring to FIGS. 13 to 16 and 28, a process of storing the medical liquid D in the reservoir 210 before the medical liquid injection device 10 is attached to a user, the medical liquid D is stored in the reservoir 210 and then injecting the medical liquid D into the user by discharging the medical liquid D from the reservoir 210 to the needle N will be described.

<Medical Liquid Storage Stage>

A user injects a medical liquid into the reservoir unit 200 of the medical liquid injection device 10 by using an external medical liquid injector (not shown). Referring to FIG. 5, before injection of a medical liquid, the plunger 230 is disposed at the front end of the reservoir 210, and the rod 410 is assembled to the connecting member 520 at the rear end of the plunger 230. At this time, since the coupler 510 does not grip the connecting member 520, the drive wheel 420 is not connected to the rod 410.

A user puts a medical liquid D to be injected in a medical liquid injector (not shown) and inserts the medical liquid injector into an inlet end of the reservoir unit 200. When the medical liquid D is injected, the plunger 230 retracts together with the connecting member 520. At this time, the resistance member 530 attached to the connecting member 520 collides with the front end 420F of the drive wheel 420 and generates a resistance force in a direction opposite to the moving direction of the connecting member 520. The medical liquid D is injected into the reservoir 210 only when a pressure high enough to overcome the resistance force is generated. Also, the medical liquid D injected into the reservoir 210 maintains a high pressure.

When the medical liquid D is injected, the air remaining inside the reservoir 210 may be primed. In detail, during the assembly of the reservoir unit 200, the air remains between the reservoir 210 and the plunger 230. When the medical liquid D is injected while the air remains in the reservoir 210, there is a risk that the air will also be injected into a user, and thus an operation of removing the air (priming operation) is needed.

When the medical liquid D starts flowing into the reservoir 210 from the medical liquid injector, the medical liquid D flows between the inner surface of the reservoir 210 and the plunger 230 and pushes out the remaining gas to the needle N. At this time, the gas may move along the guide groove 211. In other words, the gas remaining inside the reservoir 210 may be pushed by the medical liquid D flowing into the reservoir 210, guided by the guide groove 211, and discharged to the needle N. The gas passed through the needle N moves to the needle cover assembly 700, passes through the filter member 730 of the needle cover assembly 700, and is discharged to the outside. By being guided by the guide groove 211, the gas remaining inside the reservoir 210 is quickly discharged to the outside, and thus the gas in the reservoir 210 may be removed.

The first sensor unit 910A may be driven according to an amount of the medical liquid D injected into the reservoir 210.

When the plunger 230 passes the point P-1 according to the injection of the medical liquid D, the connecting member 520 contacts the first contact end 911 at the first position P1. Thereafter, when the plunger 230 passes the point P-2, the connecting member 520 contacts the second contact end 912 at the second position P2.

According to an embodiment, when the connecting member 520 electrically interconnects the first contact end 911 and the second contact end 912, a first mode is started. The first mode is a mode for waking up the medical liquid injection device 10 and pre-heat the medical liquid injection device 10, such that the medical liquid injection device 10 is immediately driven when the medical liquid injection device 10 is attached to a user. Also, the user may be notified in advance through the user terminal 20 that a pre-set first reference amount of the medical liquid D is stored in the reservoir 210, and thus the user may use the medical liquid injection device 10.

According to another embodiment, when the connecting member 520 is connected to the first contact end 911, the control module 16 recognizes the connection as a first event. When the connecting member 520 is connected to the second contact end 912, the control module 16 may recognize the connection as a second event. In other words, when the connecting member 520 contacts different contact ends, different events may be recognized and the events may be transmitted to the user.

<Attachment Stage>

As shown in FIG. 14, when the medical liquid D is stored in the reservoir 210, the medical liquid injection device 10 is attached to a user. Since a gas in the reservoir 210 is removed (priming operation is completed) through the needle cover assembly 700 in the above-described medical liquid storage stage, the needle cover assembly 700 is removed from the medical liquid injection device 10.

The user attaches the medical liquid injection device 10 to himself/herself and rotates the needle assembly 100, thereby inserting the needle N and a cannula into the skin. The needle N is inserted into the skin together with the cannula and may lead the cannula to be inserted into the skin.

Thereafter, the needle N is withdrawn from the skin, but remains connected to the cannula. When the user further rotates the needle assembly 100, the needle N moves upward while the cannula is inserted into the skin. The cannula and the needle N are at least partially connected to each other and form and maintain a path through which the medical liquid moves.

<Medical Liquid Injection Stage—Second Mode>

The driving module 300 and the driving unit 400 are driven at substantially the same time as the cannula and the needle N are inserted into the user. In a second mode, the medical liquid injection device 10 may inject the medical liquid D into the user according to a set cycle and a set injection amount.

When the user rotates the needle assembly 100 to insert the needle N and the cannula into the skin, the trigger member 600 drives the driving module 300. When the driving module 300 is driven, the connector CN rotates around the rotation axis and rotates the drive wheel 420. The connector CN may rotate the drive wheel 420 tooth-by-tooth while alternately applying forces to the first connection end 421 and the second connection end 422.

When the user rotates the needle assembly 100, the trigger member 600 may activate the coupler 510 as shown in FIG. 7. When the coupler 510 grips the outer portion of the connecting member 520, the drive wheel 420, the coupler 510, and the connecting member 520 are integrated into one body. Therefore, when the drive wheel 420 rotates, the connecting member 520 also rotates, and the rod 410 moves forward.

When the rod 410 moves forward, the plunger 230 may also move forward, and the medical liquid may be discharged to the needle N. Therefore, the medical liquid may be injected into the user according to a set driving cycle and a set driving speed of the driving module 300.

At this time, the second sensor unit 920 may detect rotation of the connector CN. The 1A contact end 921 and the 2A contact end 922 of the second sensor unit 920 alternately contact corresponding ends of the connector CN, respectively. The second sensor unit 920 senses contact between the 1A contact end 921 and a first end of the connector CN and senses contact between the 2A contact end 922 and a second end of the connector CN.

According to an embodiment, when the contact end of the second sensor unit 920 contacts the connector CN, the second sensor unit 920 may sense an electrical signal. According to another embodiment, when the contact end of the second sensor unit 920 contacts the connector CN, the second sensor unit 920 may sense an impact signal according to the contact.

The second sensor unit 920 may determine whether the driving module 300 and the connector CN are driven based on data obtained by detecting rotation of the connector CN, determine whether the drive wheel 420 is driven by using the connector CN, measure a rotational angle and/or a rotational speed of the drive wheel 420, or measure a moving distance of the plunger 230 and an injection amount of the medical liquid based on the rotation of the drive wheel 420.

When the drive wheel 420 rotates, the encoder unit 930 may measure a rotational angle and a rotational speed of the drive wheel 420. The 1B contact end 931 maintains electrical contact with the cover end 933A. Meanwhile, although the 2B contact end 932 maintains electrical contact with the teeth end 933B, when the 2B contact end 932 is separated from the teeth end 933B, the electrical contact may be released.

The encoder unit 930 may measure data related to rotation of the drive wheel 420 by measuring an electrical connection signal and/or an electrical release signal. The control module 16 may calculate the rotational angle and the rotational speed of the drive wheel 420 based on the data measured by the encoder unit 930 and calculate a moving distance of the plunger 230 and a discharge amount of the medical liquid based on the rotational angle and the rotational speed of the drive wheel 420.

<Medical Liquid Injection Stage—Third Mode>

When the plunger 230 is located at the position P-2 and the connecting member 520 is located at the second position P2, the first contact end 911 and the second contact end 912 are electrically separated in the first sensor unit 910A. The control module 16 may activate a third mode when the first sensor unit 910A is electrically released.

In the third mode, the control module 16 may transmit an alarm signal indicating that a stored amount of a medical liquid corresponds to a second reference amount to the user through the user terminal 20, the controller 30, and/or the alarm unit 800. The second reference amount may be defined as an amount of a medical liquid recognized by the driving module 300 at the time of activation of the third mode. The control module 16 may inform the user that the amount of the medical liquid remaining in the reservoir 210 is a pre-set second reference amount, and thus the user may prepare to replace the medical liquid injection device 10.

According to an embodiment, the first reference amount may be set to be the same storage amount of the medical liquid as the second reference amount. When the connecting member 520 contacts or releases contact with the second contact end 912 as the plunger 230 moves forward or backward, the position of the plunger 230 in the reservoir 210 in both cases are the same, and thus the first reference amount and the second reference amount may be set to be identical to each other.

According to another embodiment, the first reference amount may be set to be a greater storage amount of the medical liquid than the second reference amount. The first reference amount is a reference value set for operating in the first mode, and may be set to be substantially equal to an amount of a medical liquid stored in the reservoir 210. The second reference amount is an amount of a medical liquid recognized by the driving module 300 at the time of initiation of the third mode and may be set to be smaller than an actual amount of the medical liquid remaining in the reservoir 210 to have a margin.

Since the second reference amount is set to be smaller than an actual amount of the medical liquid stored in the reservoir 210, the reservoir 210 has a margin corresponding to a difference between the actual amount of the medical liquid remaining in the reservoir 210 and the second reference amount. Even when the medical liquid injection device 10 informs that there is no medical liquid, the medical liquid remaining in the reservoir 210 may be further used, thereby eliminating a sudden discontinuation of the medical liquid or an accident. As a result, the safety of the medical liquid injection device 10 may be improved.

Since a remaining amount of a medical liquid is important in the third mode, the control module 16 may calculate an injected amount of the medical liquid and an amount of the medical liquid remaining in the reservoir 210 very precisely in the third mode. In the third mode, based on data obtained by the second sensor unit 920 and the encoder unit 930, the control module 16 may accurately measure the rotational angle of the drive wheel 420 and the moving distance of the plunger 230, thereby precisely calculating a discharged amount of the medical liquid and an amount of the medical liquid remaining in the reservoir 210. The remaining amount of the medical liquid precisely calculated in the third mode may be transmitted to the user in real time, and thus the user may recognize the risk.

According to an embodiment, the medical liquid injection device 10 may accurately count the amount of the medical liquid remaining in the reservoir 210 only in the third mode. In the second mode, since the amount of the medical liquid stored in the reservoir 210 exceeds a pre-set range (i.e., the second reference amount), the amount of the medical liquid stored in the reservoir 210 is not precisely measured. However, in the third mode, the amount of the medical liquid stored in the reservoir 210 may be measured precisely. Since the amount of medical liquid stored in the medical liquid injection device 10 is accurately measured only at the level at which an alarm is needed, the control load of the medical liquid injection device 10 may be reduced.

The medical liquid injection device 10 according to an embodiment of the present disclosure may increase safety by discharging a gas discharged to the needle N to the outside. The filter member 730 of the needle cover assembly 700 may discharge the gas discharged from the reservoir 210 to the needle N to the outside. Also, the filter member 730 of the needle cover assembly 700 does not transmit the medical liquid D therethrough. Therefore, when the needle cover assembly 700 is filled with the medical liquid D, the needle cover assembly 700 protrudes convexly, thereby indicating whether the medical liquid D is stored therein.

The medical liquid injection device 10 according to an embodiment of the present disclosure may guide an injection needle to be inserted precisely into a pre-set position to inject a medical liquid, thereby safely storing the medical liquid in the reservoir 210. When the injection needle of the medical liquid injector NI is inserted into the reservoir 210 to inject a medical liquid, the needle of the medical liquid injector NI may be stably and precisely inserted into a pre-set position according to the guidance of the guide cap 250.

In the medical liquid injection device 10 according to an embodiment of the present disclosure, when the injection needle is inserted to inject a medical liquid, foreign substances are not generated due to scratches, and thus high safety of the medical liquid injection device may be secured. The rigidity of the guide cap 250 is set to be greater than the rigidity of the injection needle of the medical liquid injector NI. Even when the injection needle scratches the guide cap 250, foreign substances like debris are not generated from the guide cap 250, and thus a medical liquid may be safely stored in the reservoir 210.

The medical liquid injection device 10 according to an embodiment of the present disclosure may minimize contact with foreign substances, and a user may easily insert the injection needle of the medical liquid injector NI into the reservoir 210. The guide cap 250 may be installed at a certain depth from the bottom surface of the medical liquid injection device 10 to block introduction of foreign substances from the external environment. Also, since the guide cap 250 is exposed to be visible by a user from the outside, the user may easily and simply insert the injection needle of the medical liquid injector NI.

The medical liquid injection device 10 according to an embodiment of the present disclosure may guide an injection needle to be inserted precisely into a pre-set position to inject a medical liquid, thereby safely storing the medical liquid in the reservoir 210. When the injection needle of the medical liquid injector NI is inserted into the reservoir 210 to inject a medical liquid, the needle of the medical liquid injector NI may be stably and precisely inserted into a pre-set position according to the guidance of the guide cap 250A.

In the medical liquid injection device 10 according to an embodiment of the present disclosure, when the injection needle is inserted to inject a medical liquid, foreign substances are not generated due to scratches, and thus high safety of the medical liquid injection device may be secured. The rigidity of the guide cap 250A is set to be greater than the rigidity of the injection needle of the medical liquid injector NI. Even when the injection needle scratches the guide cap 250A, foreign substances like debris are not generated from the guide cap 250A, and thus a medical liquid may be safely stored in the reservoir 210.

According to the medical liquid injection device 10 according to an embodiment of the present disclosure, a user may easily insert the injection needle of the medical liquid injector NI into the reservoir 210. Since a sealing member includes a transparent or semi-transparent material and the guide cap 250A is exposed to be visible by a user from the outside, the user may easily and simply insert the injection needle of the medical liquid injector NI.

The technical spirit of the present disclosure should not be construed to the above-described embodiments, and not only the claims to be described later, but also anything equivalent to or equivalently modified from these claims fall within the scope of the spirit of the present disclosure.

According to an embodiment of the present disclosure, a medical liquid injection device may be applied to various industrially applicable devices. The medical liquid injection device may be applied to devices that deliver various medical liquids.

What is claimed is:

1. A medical liquid injection device comprising:
a base body;
a needle assembly mounted on the base body;
a reservoir fluidly connected to the needle assembly, the reservoir having an inlet end for injecting a medical liquid and an outlet end connected to a needle of the needle assembly, wherein the reservoir includes a guide groove that interconnects the inlet end and the outlet end;
a driving unit configured to linearly move a plunger disposed inside the reservoir when the medical liquid is discharged through the needle; and
a needle cover assembly mounted on the needle assembly, the needle cover assembly including a filter that allows air to pass through but prevents the medical liquid from passing through:
wherein the guide groove is disposed on a front surface of the reservoir facing the plunger; and
wherein the guide groove is configured to guide air remaining in the reservoir to the filter via the outlet end when the medical liquid is injected into the reservoir with the plunger positioned on the front surface, and subsequently guide the medical liquid to the filter.

2. The medical liquid injection device of claim 1, wherein:
a portion of the guide groove is disposed to be inclined along the front surface of the reservoir.

* * * * *